US 10,722,349 B2

(12) United States Patent
White et al.

(10) Patent No.: US 10,722,349 B2
(45) Date of Patent: Jul. 28, 2020

(54) ADJUSTABLE PROSTHETIC HEART VALVE

(71) Applicant: Medtronic Vascular, Inc., Santa Rosa, CA (US)

(72) Inventors: Frank White, Ballybrit (IE); Paraic Frisby, Ballybrit (IE); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 64 days.

(21) Appl. No.: 15/834,338

(22) Filed: Dec. 7, 2017

(65) Prior Publication Data
US 2019/0175338 A1 Jun. 13, 2019

(51) Int. Cl.
*A61F 2/24* (2006.01)
*A61F 2/00* (2006.01)

(52) U.S. Cl.
CPC .......... *A61F 2/2409* (2013.01); *A61F 2/0077* (2013.01); *A61F 2/2418* (2013.01); *A61F 2210/0004* (2013.01); *A61F 2210/0014* (2013.01); *A61F 2220/0008* (2013.01); *A61F 2220/0016* (2013.01); *A61F 2220/0041* (2013.01); *A61F 2230/0006* (2013.01); *A61F 2230/0008* (2013.01); *A61F 2230/0013* (2013.01); *A61F 2250/001* (2013.01); *A61F 2250/0007* (2013.01); *A61F 2250/0008* (2013.01); *A61F 2250/0067* (2013.01)

(58) Field of Classification Search
CPC ........ A61F 2/24; A61F 2/2409; A61F 2/2418; A61F 2/2445; A61F 2/2442; A61F 2/2448; A61F 2/2451
See application file for complete search history.

(56) References Cited

U.S. PATENT DOCUMENTS

| | | | |
|---|---|---|---|
| 9,492,276 B2 * | 11/2016 | Lee | ....................... A61F 2/2472 |
| 9,585,751 B2 | 3/2017 | Morriss et al. | |
| 9,655,722 B2 | 5/2017 | Morriss et al. | |
| (Continued) | | | |

FOREIGN PATENT DOCUMENTS

| | | |
|---|---|---|
| FR | 3043907 A1 | 5/2017 |
| WO | 2010079426 A1 | 7/2010 |

OTHER PUBLICATIONS

International Search Report and Written Opinion, PCT/US2018/064052, dated Feb. 15, 2019 (13 pages).

*Primary Examiner* — Seema Mathew
(74) *Attorney, Agent, or Firm* — Dicke, Billig & Czaja, PLLC

(57) ABSTRACT

A prosthetic valve including an inner frame, an outer frame, and a connection assembly interconnecting the frames. The inner frame defines an interior volume for receiving a valve structure within the interior volume. The outer frame surrounds the inner frame. The inner and outer frames are each configured to be transitionable between compressed and expanded conditions. The prosthetic heart valve provides a initial deployed state in which the inner and outer frames are in the expanded condition, and a radial shape of the outer frame is adjustable via the connection assembly to a final deployed state. A shape of the outer frame can be adjusted upon implant to enable radial anchoring at the native annulus, while addressing possible non-uniformities of the native annulus and possible anatomical concerns such as LVOT obstruction.

20 Claims, 22 Drawing Sheets

(56) References Cited

U.S. PATENT DOCUMENTS

| | | | |
|---|---|---|---|
| 10,201,419 B2* | 2/2019 | Vidlund | A61F 2/2418 |
| 2009/0248148 A1* | 10/2009 | Shaolian | A61F 2/2448 |
| | | | 623/2.37 |
| 2010/0185275 A1* | 7/2010 | Richter | A61F 2/2409 |
| | | | 623/2.11 |
| 2010/0280607 A1* | 11/2010 | Milo | A61F 2/2448 |
| | | | 623/2.37 |
| 2013/0116780 A1* | 5/2013 | Miller | A61F 2/2445 |
| | | | 623/2.36 |
| 2013/0166017 A1* | 6/2013 | Cartledge | A61F 2/93 |
| | | | 623/1.15 |
| 2015/0039080 A1* | 2/2015 | Figulla | A61F 2/2457 |
| | | | 623/2.1 |
| 2015/0119982 A1 | 4/2015 | Quill et al. | |
| 2016/0008130 A1* | 1/2016 | Hasin | A61F 2/2418 |
| | | | 623/2.37 |
| 2016/0216026 A1 | 7/2016 | Quill et al. | |
| 2016/0256274 A1* | 9/2016 | Hayoz | A61F 2/2445 |
| 2017/0007401 A1* | 1/2017 | Hayoz | A61F 2/2445 |
| 2017/0095331 A1* | 4/2017 | Spenser | A61F 2/2412 |
| 2017/0216023 A1 | 8/2017 | Lane et al. | |
| 2018/0333259 A1* | 11/2018 | Dibie | A61F 2/2418 |
| 2020/0015970 A1* | 1/2020 | Solem | A61F 2/2445 |

* cited by examiner

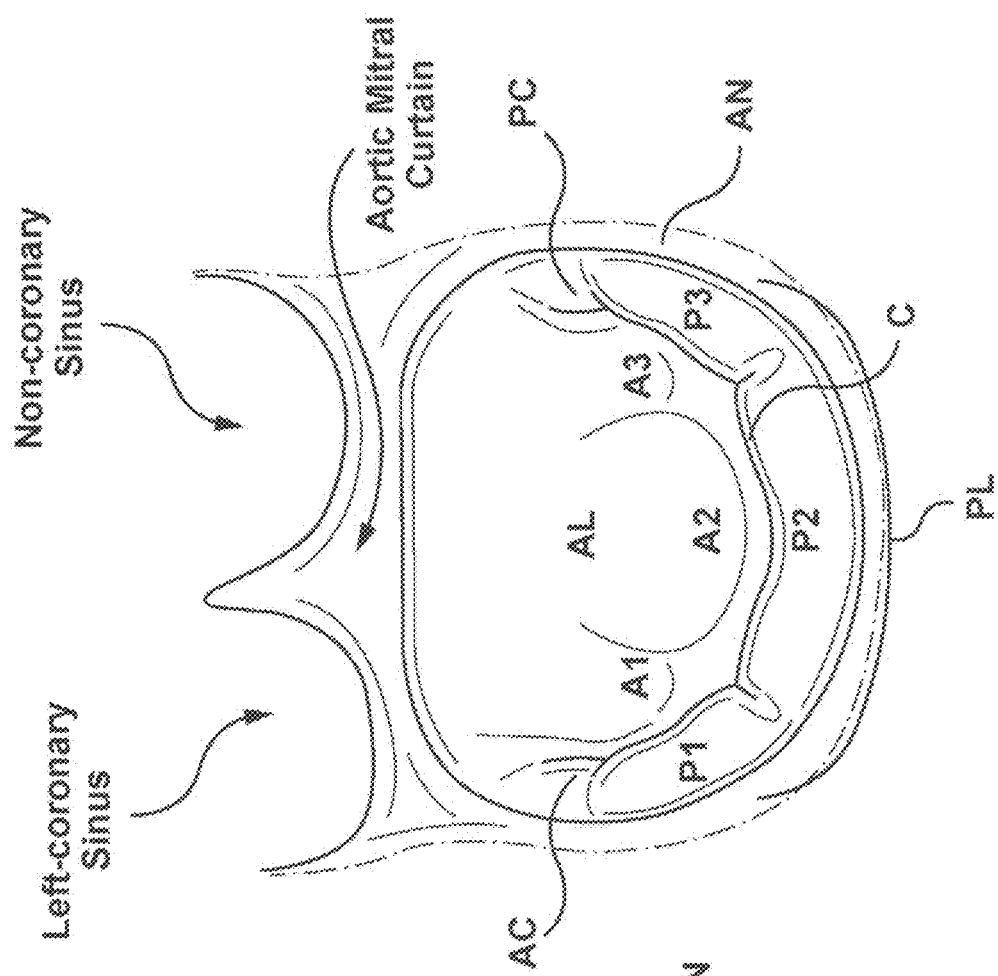
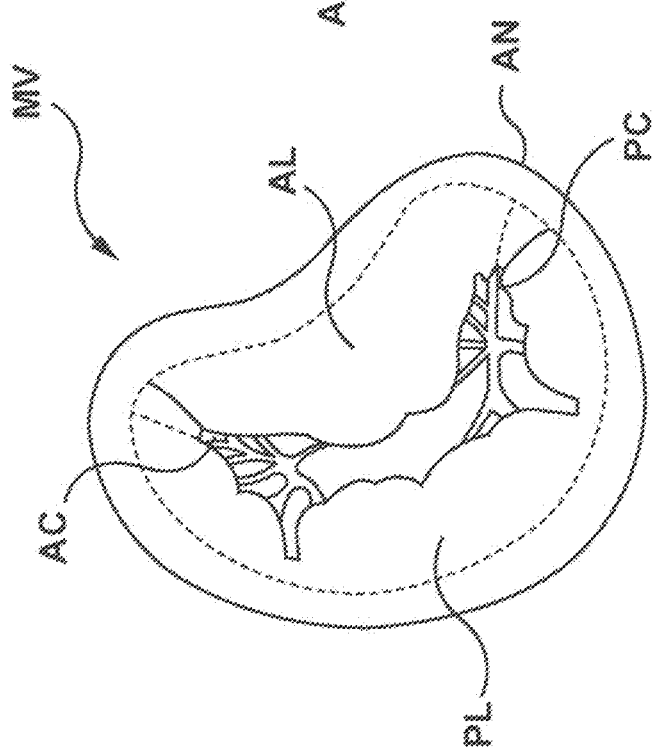
FIG. 3B
FIG. 3A

ADJUSTABLE PROSTHETIC HEART VALVE

BACKGROUND

The present disclosure relates to prosthetic heart valves. More particularly, it relates to prosthetic heart valves appropriate for transcatheter delivery to a target site and adjustable to a shape of the target site, such as a native mitral valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. The tricuspid valve, also known as the right atrio-ventricular valve, is a tri-flap valve located between the right atrium and the right ventricle. The mitral valve, also known as the bicuspid or left atrio-ventricular valve, is a dual-flap valve located between the left atrium and the left ventricle.

As with other valves of the heart, the mitral valve is a passive structure in that it does not itself expend any energy and does not perform any active contractile function. The mitral valve includes an annulus that provides attachment for the two leaflets (anterior leaflet and posterior leaflet) that each open and close in response to differential pressures on either side of the valve. The leaflets of the mitral valve are dissimilarly shaped. The anterior leaflet is more firmly attached to the annulus, and is somewhat stiffer than the posterior leaflet (that is otherwise attached to the more mobile posterior lateral mitral annulus). The anterior leaflet protects approximately two-thirds of the valve. The anterior leaflet takes up a larger part of the annulus and is generally considered to be "larger" than the posterior leaflet (although the posterior leaflet has a larger surface area). In a healthy mitral valve, then, the anterior and posterior leaflets are asymmetric.

Ideally, the leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

The actual shape and configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Moreover, the stent frame must have a robust design capable of traversing the tortuous path leading to the native valve annulus site. These constraints, as well as other delivery obstacles such as difficulties in precisely locating and rotationally orienting the prosthetic valve relative to the native annulus, dictate that in some instances, it is beneficial to utilize a valve structure with the prosthesis that purposefully differs from the native (healthy) valve structure or leaflets. For example, the transcatheter prosthetic heart valve may incorporate a symmetric valve structure for replacing an asymmetric native valve, an asymmetric valve structure to replace a symmetric native valve, a valve structure having a greater or lesser number of leaflets than the native valve, a valve structure having leaflet shapes differing from the native valve, etc. These same design choices can arise in the context of other intraluminal prosthetic valves.

While the so-configured prosthetic valve can thus achieve the intended benefits (such as ease of implant) along with long term viable performance as a functioning valve, in some instances other concerns may arise. For example, challenges remain for preventing movement and/or migration of the prosthetic valve that could occur during the cardiac cycle and to prevent leakage between the implanted prosthetic valve and the surrounding tissue (paravalvular leakage). Further, the anchoring forces generated by a transcatheter prosthetic heart valve upon deployment may lead to interference with flow or conduction channels within the heart. For example, the design of a prosthetic mitral valve must account for the elliptical shape, dynamic nature and complex subvalvular apparatus associated with the native mitral valve and proximate anatomy. The requisite radial forces generated by many transcatheter prosthetic mitral valve designs for achieving desired anchoring with this native mitral valve anatomy can lead to obstruction of the left ventricular outflow tract (LVOT) and/or negatively impact the coronary sinus.

SUMMARY

The inventors of the present disclosure recognized that a need exists for transcatheter prosthetic heart valves, such as transcatheter prosthetic mitral valves, that address one or more of the above-mentioned problems.

Some aspects of the present disclosure relate to a prosthetic heart valve including an inner frame, an outer frame, and a connection assembly. The inner frame defines an interior volume, and is configured to receive a valve structure within the interior volume. The outer frame surrounds the inner frame. The inner and outer frames are each configured to be transitionable between a compressed condition and an expanded condition. The connection assembly interconnects the inner and outer frames. The prosthetic heart valve is configured to provide an initial deployed state in which the inner and outer frames are in the expanded condition, and a radial shape of the outer frame is adjustable via the connection assembly to provide a final deployed state. With this construction, a shape of the outer frame can be adjusted upon implant to enable radial anchoring at the native annulus, while addressing possible non-uniformities of the native annulus and possible anatomical concerns such as LVOT obstruction. In some embodiments, the connection assembly includes a plurality of connecting members extending between an interior of the outer frame and an exterior of the inner frame. In other embodiments, the connection assembly includes a plurality of arm pairs, with each arm pair having a first arm projecting from an exterior of the inner frame and a second arm projecting from an interior of the outer frame. The arm pairs are operable to adjust a spacing between the inner and outer frames at a location of the respective arm pair.

Other aspects of the present disclosure are directed toward a method of implanting a prosthetic heart valve. The method includes arranging a prosthetic heart valve in a delivery state. The prosthetic heart valve includes an inner frame, a valve structure, an outer frame, and a connection assembly. The inner frame defines an interior volume. The valve structure is mounted to the inner frame and is disposed within the interior volume. The outer frame surrounds the inner frame. The inner and outer frames are each configured to be transitionable between a compressed condition and an expanded condition. The connection assembly interconnects the inner and outer frames. The delivery state includes the inner and outer frames in the compressed condition. The prosthetic heart valve is delivered through a patient's vasculature to a native heart valve target site. The prosthetic heart valve is deployed at the target site such that the prosthetic heart valve transitions to an initial deployed state in which the inner and outer frames are in the expanded condition. A radial shape of the outer frame is adjusted from the deployed state to a final deployed state. With this approach, the adjusted radial shape of the outer frame can be set by a clinician in accordance with anatomical features of the native heart valve target site. In some embodiments, the radial shape of the outer frame is adjusted by rotating the inner frame relative to the outer frame. In some embodiments, the native heart valve target site is a native mitral valve.

BRIEF DESCRIPTION OF THE DRAWINGS

FIG. 3A is a schematic illustration of a superior view of a mitral valve isolated from the surrounding heart structures and showing the annulus and native leaflets;

FIG. 3B is a schematic illustration of a superior view of a mitral valve, aortic mitral curtain and portions of the aortic valve isolated from the surrounding heart structures and showing regions of the native mitral valve leaflets;

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

The following detailed description of prosthetic valves of the present disclosure is merely exemplary in nature and is not intended to limit the disclosure or the application and uses of the prosthetic valves of the present disclosure. Although the description is in the context of treatment of heart valves such as the mitral valve, the prosthetic valves of the present disclosure also may be used in any other body passageways, organs, etc., where it is deemed useful. Furthermore, there is no intention to be bound by any expressed or implied theory presented in the present disclosure. Some embodiments of the present disclosure can be therapeutically combined with many known surgeries and procedures, for example, such embodiments can be combined with known methods of accessing the valves of the heart such as the mitral valve with antegrade approaches, such as a transseptal or transatrial approach, and combinations thereof.

Figure 1:
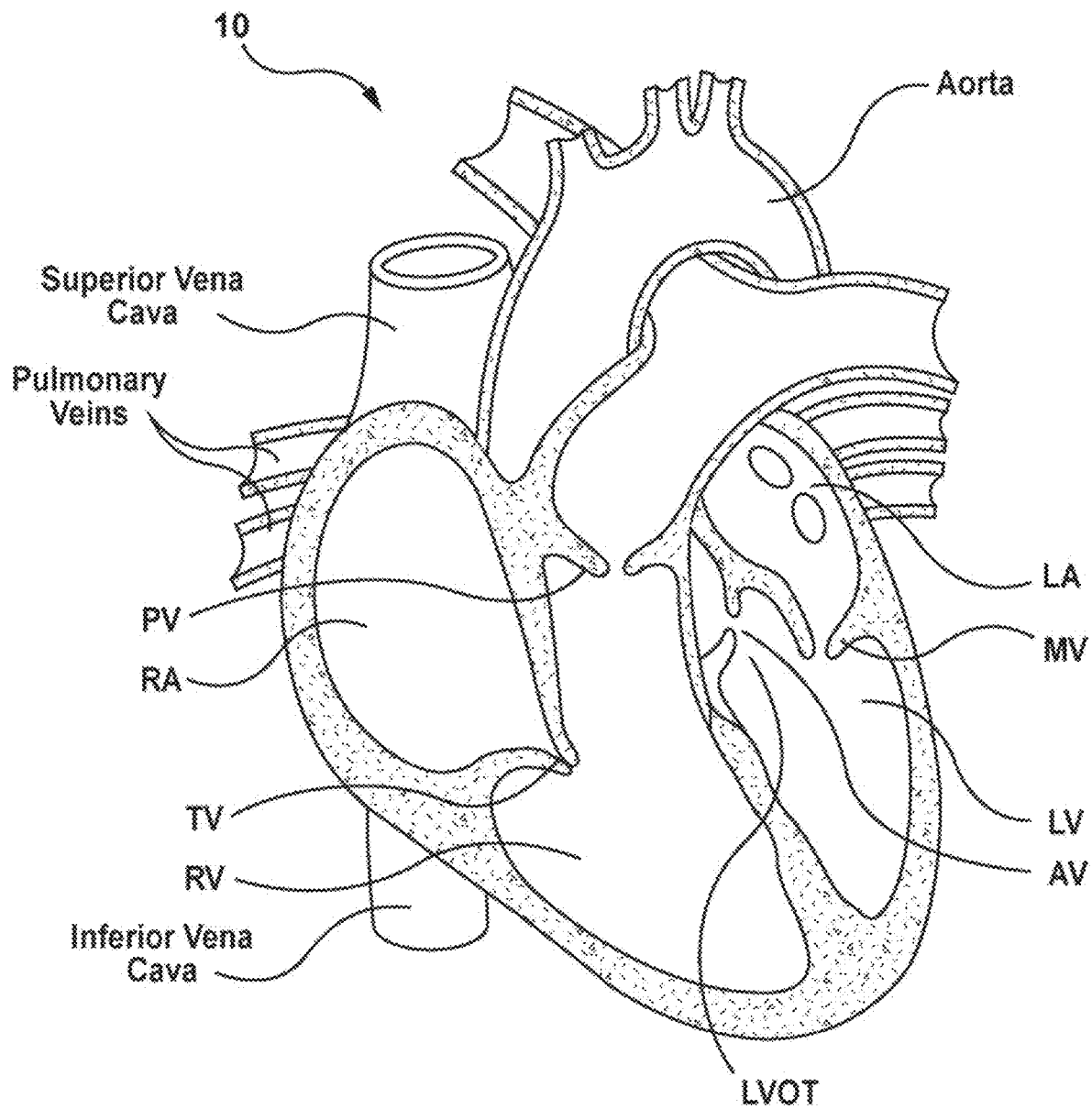
FIG. 1 is a schematic sectional illustration of a mammalian heart having native valve structures.
Figure 2A:
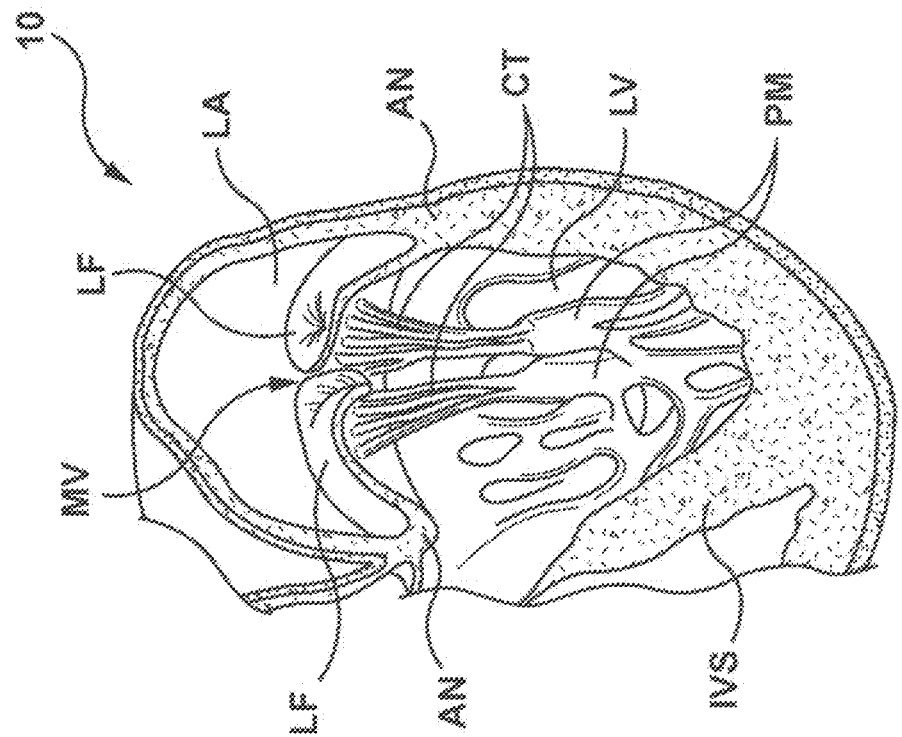
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
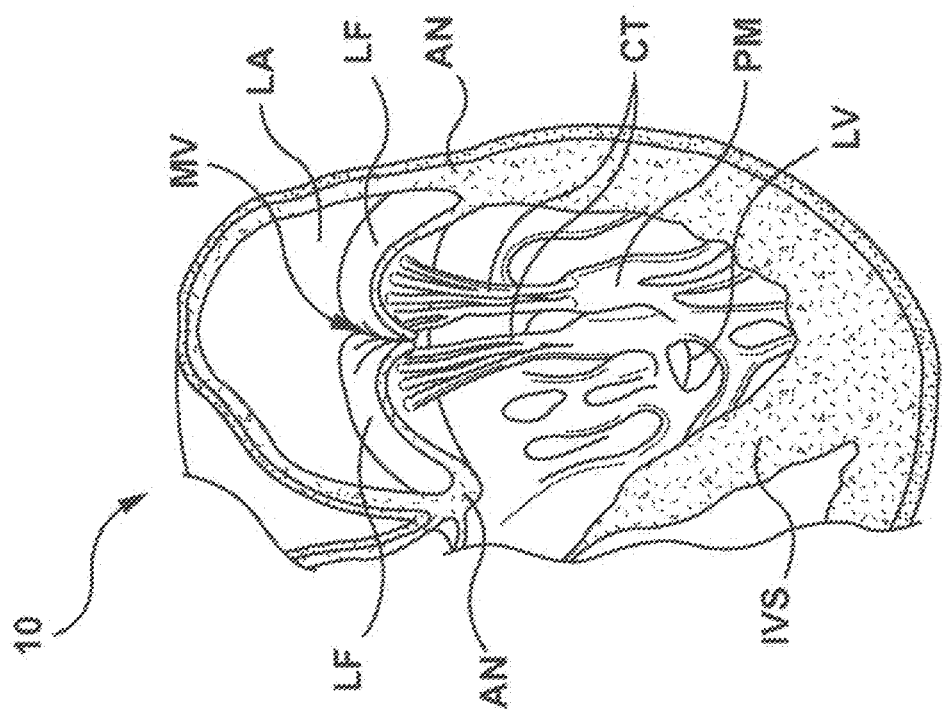
FIG. 2B is a schematic sectional illustration of the left ventricle of the heart having a prolapsed mitral valve in which the leaflets do not sufficiently coapt and which is suitable for replacement with various embodiments of prosthetic heart valves in accordance with principles of the present disclosure.

In a healthy heart, the leaflets LF of the mitral valve MV meet evenly at the free edges or "coapt" to close and prevent back flow of blood during contraction of the left ventricle LV (FIG. 2A). Referring to FIG. 2A, the leaflets LF attach the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral leaflets LF are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left atrium LA into the left ventricle LV will occur. Several structural defects can cause the mitral leaflets LF to prolapse such that regurgitation occurs, including ruptured chordae tendinae CT, impairment of papillary muscles PM (e.g., due to ischemic heart disease), and enlargement of the heart and/or mitral valve annulus AN (e.g., cardiomyopathy).

FIG. 3 is a superior view of a mitral valve MV isolated from the surrounding heart structures and further illustrating the shape and relative sizes of the mitral valve leaflets AL, PL and annulus AN. FIG. 3B is a schematic illustration of a superior view a mitral valve MV, aortic mitral curtain and portions of the aortic valve AV isolated from the surrounding heart structures and showing regions of the native mitral valve leaflets AL, PL. With reference to FIGS. 3A and 3B together, the mitral valve MV includes an anterior leaflet AL with segments or scallops A1, A2, and A3 that meet and oppose respective segments or scallops P1, P2 and P3 of a posterior leaflet PL at a coaptation line C (FIG. 3B) when closed. FIGS. 3A and 3B together further illustrate the shape and relative sizes of the leaflets AL, PL of the mitral valve. As shown, the mitral valve MV generally has a "D" or kidney-like shape and the line of coaptation C is curved or C-shaped, thereby defining a relatively large anterior leaflet AL and substantially smaller posterior leaflet PL. Both leaflets appear generally crescent-shaped from the superior or atrial side, with the anterior leaflet AL being substantially wider in the middle of the valve at the A2 segment thereof than the posterior leaflet at the P2 segment thereof (e.g., comparing segments A2 and P2, FIG. 3B). As illustrated in FIGS. 3A and 3B, at the opposing ends of the line of coaptation C, the leaflets join together at corners called the anterolateral commissure AC and posteromedial commissure PC, respectively. When the anterior leaflet AL and posterior leaflet PL fail to meet (FIG. 3A), regurgitation between the leaflets AL, PL or at commissures AC, PC at the corners between the leaflets can occur.

Referring to FIGS. 3A and 3B, the mitral valve annulus AN is a fibrotic ring that consists of an anterior part and a posterior part. The aortic-mitral curtain (FIG. 3B) is a fibrous structure that connects the anterior mitral annulus AN intimately with the aortic valve annulus (at the level of the left and non-coronary cusps or sinuses). The posterior part of the mitral annulus AN is not reinforced by other structures of the heart and is rather discontinuous (making it prone to dilatation). The leaflets AL, PL and the annulus AN are comprised of different types of cardiac tissue having varying strength, toughness, fibrosity, and flexibility. Furthermore, the mitral valve MV may also comprise a region of tissue interconnecting each leaflet to the annulus AN (indicated at dashed line in FIG. 3A).

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, work in relation to embodiments suggests that patients may have a long dimension across the annulus and a short dimension across the annulus with or without well-defined peak and valley portions, and the methods and device as described herein can be configured accordingly.

Figure 4:
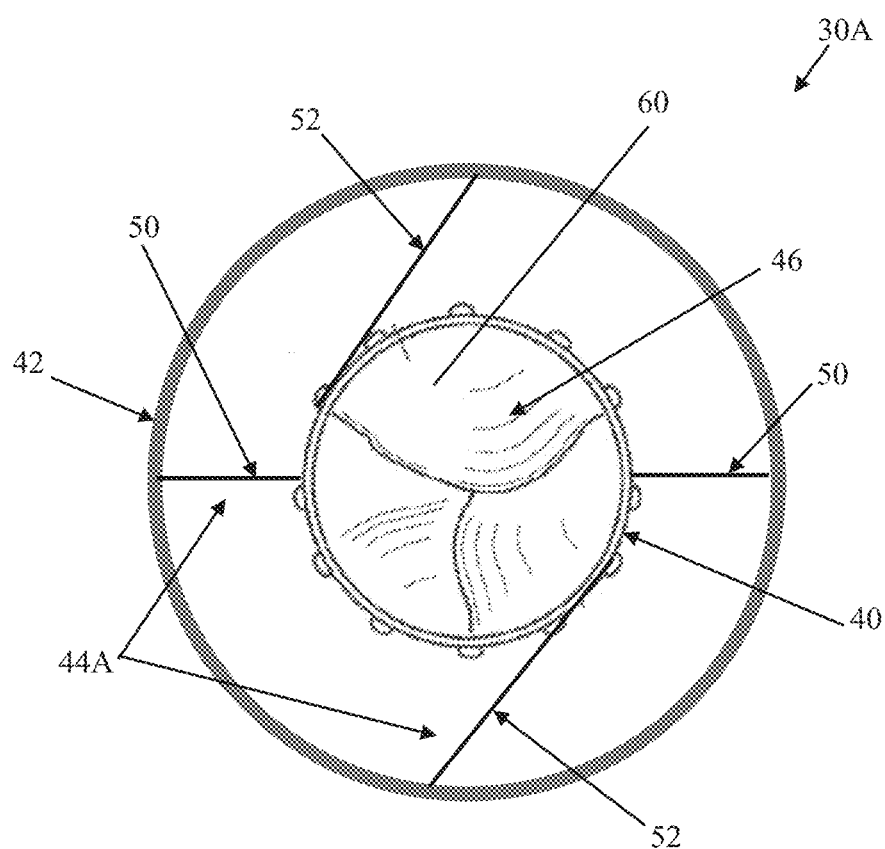
FIG. 4 is a simplified plan view of a prosthetic heart valve in accordance with principles of the present disclosure and in an initial deployed state.
Figure 5:
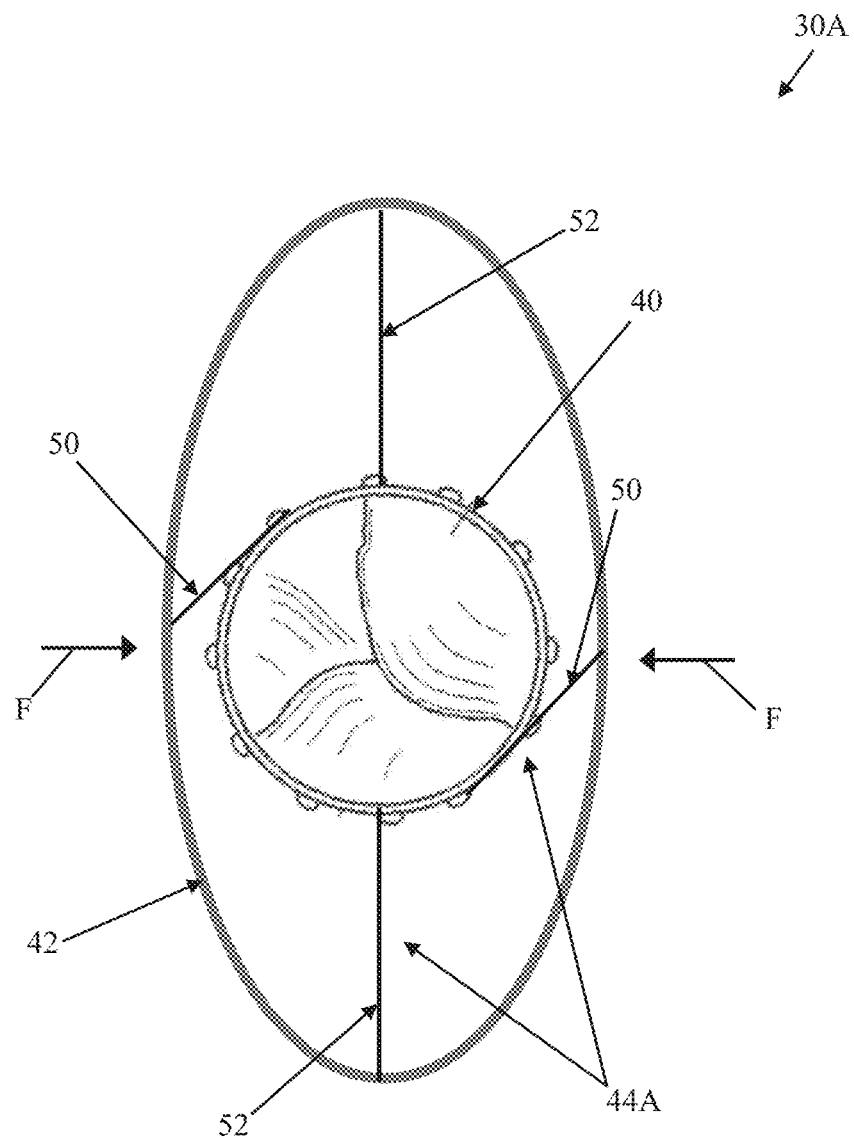
FIG. 5 is a simplified plan view of the prosthetic heart valve of FIG. 4 in a final deployed state.

Against the above background, some embodiments of the present disclosure relate to a transcatheter prosthetic heart valve configured for deployment and anchoring at the native mitral valve anatomy. One embodiment of a prosthetic heart valve 30A in accordance with principles of the present disclosure is schematically illustrated in FIGS. 4 and 5 (with FIG. 4 representing an initial deployed state and FIG. 5 representing a final deployed state). The prosthetic heart valve 30A includes an inner frame 40, an outer frame 42, a connection assembly 44A (referenced generally) and a valve structure 46. Details on the various components are provided below. In general terms, the inner and outer frames 40, 42 are each configured to be transitionable between a compressed condition and an expanded condition. As a point of reference, FIG. 4 represents each of the inner and outer frames 40, 42 in a corresponding expanded condition, free of external forces (e.g., in the representation of FIG. 4, there are no external forces placed upon the outer frame 42, allowing the outer frame 42 to freely assume the shape shown). The connection assembly 44A interconnects the inner and outer frames 40, 42. The valve structure 46 is supported by or mounted to the inner frame 40. The prosthetic heart valve 30A is configured to provide the initial deployed state in which the inner and outer frames 40, 42 are in the expanded condition, and a radial shape of the outer frame 42 is adjustable via the connection assembly 44A as described below to achieve a desired, final deployed state such as shown in FIG. 5. The prosthetic heart valve 30A can optionally include one or more additional components, such as a skirt, structures that facilitate transcatheter delivery, etc.

The inner frame 40 can be or include a stent or stent-like construction defining an interior volume sized and shaped to receive the valve structure 46. In some non-limiting embodiments, for example, the inner frame 40 can be akin to the stent frame utilized with a transcatheter mitral valve replacement available from Twelve Inc. under the trade designation "INTREPID". Other stent structures or assemblies are equally acceptable. Regardless, when constructed as stent or stent structure, the inner frame 40 has a normal, expanded condition or arrangement and is collapsible to a compressed condition or arrangement for loading within a delivery device. The inner frame 40 is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The inner frame 40 can be laser-cut from a single piece of material, or can be assembled from a number of discrete components.

The inner frame 40 can have a lattice or cell-like structure. The inner frame 40 can be made from stainless steel, a pseudo-elastic metal such as a nickel titanium alloy or Nitinol™, or a so-called super alloy, which may have a base metal of nickel, cobalt, chromium, or other metal. In some embodiments, the inner frame 40 is self-expanding to return to the normal expanded condition from the compressed condition. "Self-expanding" as used herein means that the inner frame 40 has a mechanical memory to return to the normal or expanded condition. Mechanical memory can be imparted to the wire or tubular structure that forms the inner frame 40 by thermal treatment to achieve a spring temper in stainless steel, for example, or to set a shape memory in a susceptible metal allow, such as Nitinol, or a polymer, such as any of the polymers disclosed in US Application Publication No. 2004/0111111 to Lin, which is incorporated by reference herein in its entirety. In other embodiments, the inner frame 40 need not be of a self-expanding construction. For example, the inner frame 40 could be of a balloon expandable or mechanically expandable construction. Regardless, the inner frame 40 can be formatted to assume a variety of different shapes in the normal, expanded condition that may or may not correspond to the native anatomy at which the prosthetic heart valve 30A will be implanted and that may or may not be implicated by the general shapes reflected in FIG. 4 (e.g., the inner frame 40 need not have the circular-like shape in the expanded condition).

The outer frame 42 can also be or include a stent or stent-like structure akin to the descriptions above with respect to the inner frame 40. The outer frame 42 defines an interior volume appropriate for receiving the inner frame 40 (i.e., the inner and outer frames 40, 42 are sized and shaped such that the inner frame 40 is disposed within the outer frame 42). While the inner and outer frames 40, 42 can each be or include a stent or stent-like structure, a hoop strength of the outer frame 42 can be less than a hoop strength of the inner frame 40 in at least the corresponding expanded conditions for reasons made clear below. That is to say, the inner and outer frames 40, 42 can differ from one another in at least one or more of the shape, material, structure (e.g., stent cell structure), etc., such that the inner frame 40 will maintain its shape in the presence of externally-applied radial forces that are otherwise sufficient to cause the outer frame 42 to deflect or deform. For example, and as generally represented by FIG. 5, the inner and outer frames 40, 42 can be configured to have differing hoop strengths such that radial forces F applied to the outer frame 42 (in the expanded condition) cause, at least in part, the outer frame 42 to deflect or deform in shape (e.g., the outer frame 42 has assumed a more elliptical shape in FIG. 5 as compared to the more circular shape in FIG. 4 in which the radial forces F are not present), while the inner frame 40 has not overtly deflected or deformed (e.g., in the state of FIG. 5, the inner frame 40 has maintained the circular shape shown in FIG. 4).

The connection assemblies of the present disclosure can assume various forms appropriate for maintaining the inner frame 40 relative to the outer frame 42 (e.g., the inner and outer frames 40, 42 are maintained in a concentric arrangement) in a manner that permits selective manipulation of the outer frame 42 to the final deployed state of FIG. 5. In some embodiments, the connections assemblies of the present disclosure permit rotation of the inner frame 40 relative to the outer frame 42, and can transfer forces from the inner frame 40 to the outer frame 42. For example, in the non-limiting embodiment of FIG. 4, the connection assembly 44A includes a plurality of connecting members, such as first connecting members 50 and second connecting members 52, each extending between an exterior of the inner frame 40 and an interior of the outer frame 42. In some embodiments, the connecting members 50, 52 are secured to the inner frame 40 (e.g., a pivoting-typing connection) and are slidably captured relative to the outer frame 42 (e.g., an end of each of the connecting members 50, 52 interfaces with the outer frame 42 within a channel or slot (not shown)). Other attachment techniques are also acceptable (e.g., the connecting members 50, 52 can be more rigidly connecting to the outer frame 42). Regardless, the connecting members 50, 52 can be made from stainless steel, a pseudo-elastic metal such as a nickel titanium alloy or Nitinol™, or a so-called super alloy, which may have a base metal of nickel, cobalt, chromium, or other metal. In some embodiments, the connecting members 50, 52, and corresponding connection with the inner and outer frames 40, 42, are configured to facilitate the transitioning between the compressed and normal (expanded) conditions as described above. For example, the connecting members 50, 52 can have a self-expanding attribute, capable of returning to the normal expanded condition of FIG. 4 from the compressed condition (e.g., such as when the prosthetic heart valve 30A is compressed and loaded within a delivery sheath or catheter).

In addition, and as revealed by a comparison of FIGS. 4 and 5, the connecting members 50, 52 and corresponding connection with the frames 40, 42 permits the inner frame 40 to rotate relative to the outer frame 42 (the inner frame 40 has been rotated in a clockwise direction in transitioning from the state of FIG. 4 to the state of FIG. 5). In this regard, a length and/or connection format of the connecting members 50, 52 can differ, effectuating a camming like action onto the outer frame 42 with rotation of the inner frame 42. For example, a length of the first connecting members 50 can be less than a length of the second connecting members 52. In addition and/or alternatively, an arrangement of the first connecting members 50 relative to the inner and outer frames 40, 42 can differ from the arrangement of the second connecting members 52 (with the prosthetic heart valve 30A in the initial deployed state of FIG. 4). With the configuration of FIG. 4, for example, the first connecting members 50 are shorter than the second connecting members 52; although the first connecting members 50 and the second connecting members 52 have differing lengths, the connecting members 50, 52 are arranged relative to the inner and outer frames 40, 42 such that in the initial deployed state, the inner and outer frames 40, 42 assume the concentric, circular shapes as shown. With subsequent rotation of the inner frame 40 relative to the outer frame 42, and optionally in the presence of the radial forces F acting upon the outer frame 42, the optional elevated hoop strength of the inner frame 40 (as compared to the hoop strength of the outer frame 42) is transferred as a force onto the outer frame 42, causing the outer frame 42 to deform from the circular-like shape of the initial deployment state of FIG. 4 to the elliptical-like shape of the final deployed state of FIG. 5 in a cam-like fashion. In other words, a force applied by each of the connecting members 50, 52 onto the outer frame 42 varies as a function of a rotational position of the inner frame 40 relative to the outer frame 42; the first connecting members 50 pull the outer frame 42 toward the inner frame 40 at the corresponding point of connection, whereas the second camming members 52 push the outer frame 42 away from the inner frame 40 at the corresponding point of connection. While the connection assembly 44A is shown as having four connecting members 50, 52, any other number, either greater or lesser, is equally acceptable.

In some embodiments, the connection assembly 44A can include one or more components in addition to the connecting members 50, 52. For example, locking or ratchet structures or mechanisms can be provided that selectively lock the inner frame 40 relative to the outer frame 42 at various rotational positions (e.g., the locking structures or mechanisms can be configured such that the inner frame 40 can only rotate in one direction relative to the outer frame 42).

The valve structure 46 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 46 can be formed, for example, from bovine, porcine, equine, ovine and/or other suitable animal tissues. In some embodiments, the valve structure 46 can be formed, for example, from heart valve tissue, pericardium, and/or other suitable tissue. Non-limiting examples of prosthetic valves and/or prosthetic valve features that may be used in accordance with one or more embodiments of the present disclosure are described in U.S. patent application Ser. No. 14/175,100, filed Feb. 7, 2014, entitled "HEART VALVE PROSTHESIS", and which patent application is hereby incorporated by reference in its entirety to the extent that it does not conflict with the disclosure presented herein In some embodiments, the valve structure 46 can include or form one or more leaflets 60. For example, the valve structure 46 can be in the form of a tri-leaflet bovine pericardium valve, a bi-leaflet valve, or another suitable valve. In some constructions, the valve structure 46 can comprise two or three leaflets that are fastened together at enlarged lateral end regions to form commissural joints, with the unattached edges forming coaptation edges of the valve structure 46. The leaflets 60 can be fastened to a skirt that in turn is attached to the inner frame 40. Regardless, the valve structure 46 transitions between a closed state (reflected in FIG. 4), in which the valve structure 46 closes the lumen of the inner frame 40 and prevents fluid flow there through, and an open state in which the valve structure 46 permits fluid flow through the lumen.

Though not shown in FIGS. 4 and 5, the prosthetic heart valves of the present disclosure, such as the prosthetic heart valve 30A, can further include a cover (e.g., polyester skirt, tissue, etc.) that spans the space between the inner and outer frames 40, 42. Where provided, the cover is configured provide an appropriate seal to blood flow between the inner and outer frames 40, 42, and is sufficiently flexible to expand/contract with changes in shape of the outer frame 42.

Figure 6:
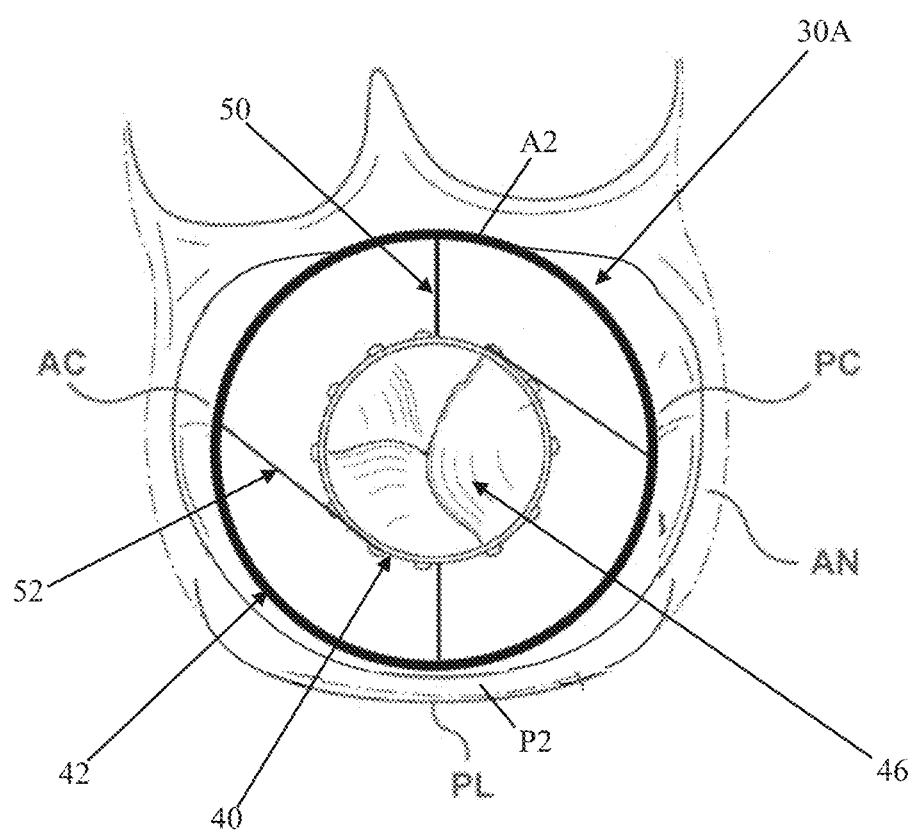
FIG. 6 is a schematic illustration of a superior view of the prosthetic heart valve of FIG. 4 in an initial deployed state at a native mitral valve.
Figure 7:
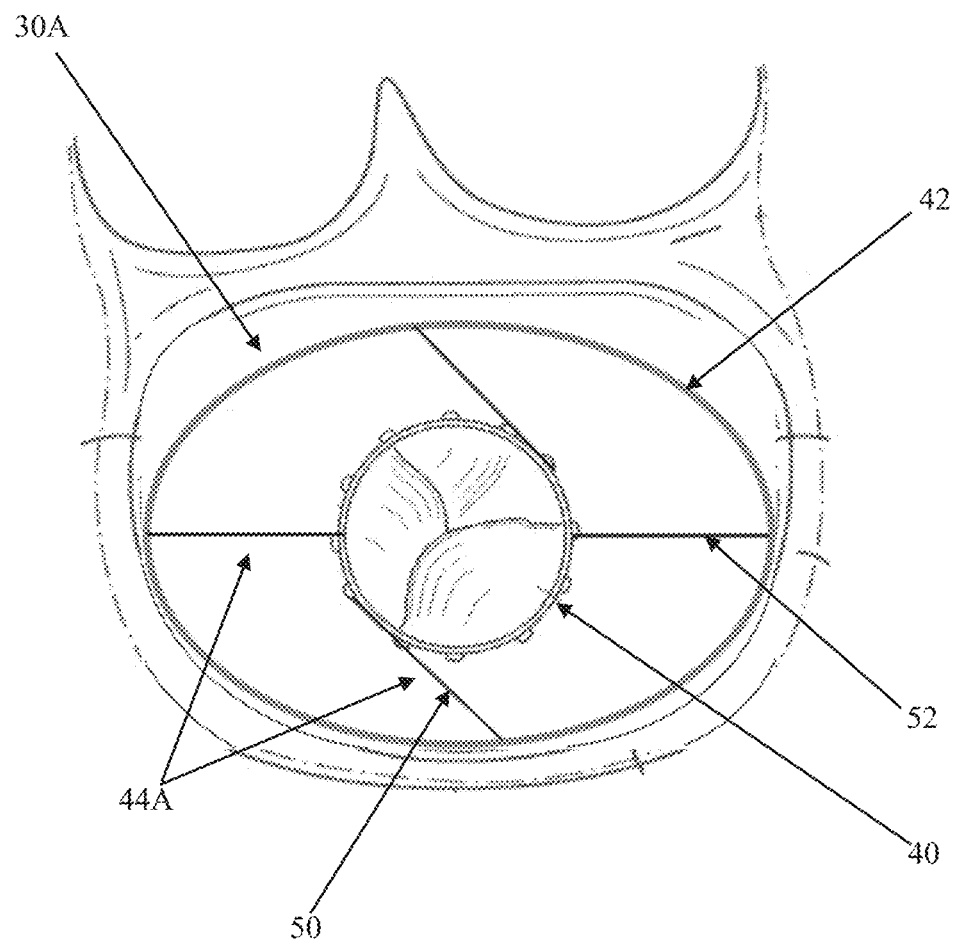
FIG. 7 is a schematic illustration of the arrangement of FIG. 6 following adjustment of a radial shape of the outer frame of the prosthetic heart valve to a final deployed state.

The prosthetic heart valve 30A can be delivered to a target site (e.g., native mitral valve anatomy) using transcatheter delivery devices as are known to those of ordinary skill. In general terms, the prosthetic heart valve 30A is radially compressed over a shaft of the delivery device, and maintained in this compressed state by an outer sheath or catheter. In this delivery state, the delivery device is manipulated to locate the prosthetic heart valve at a target site (e.g., a native heat valve). Once located at the target site, the outer sheath is withdrawn from over the prosthetic heart valve 30A (and/or the prosthetic heart valve 30A is distally advanced relative to the outer sheath), and the prosthetic heart valve 30A expands (self-expansion, balloon-caused expansion, etc.) to a deployment state. With embodiments in which the prosthetic heart valve 30A is configured and deployed for replacing a native mitral valve, some methods of the present disclosure include an initial deployed state reflected in FIG. 6. As initially deployed, the inner and outer frames 40, 42 each assume the circular-like shape as described above. There is radial interference between the outer frame 42 and anatomy of the mitral valve MV at segments A2, P2, but minimal or no interference between the outer frame 42 and the commissures AC, PC (as well as with the LVOT (FIG. 1)). The inner frame 40 is then rotated relative to the outer frame 42 (e.g., the delivery device can include a tool linked to features provided with or on the inner frame 40 that facilitate user rotation of the inner frame 40) to transition the prosthetic heart valve 30A from the initial deployed state to the final deployed state of FIG. 7. Interference between the outer frame 42 and the mitral valve segments A2, P2 prevents the outer frame 42 from rotating with rotation of the inner frame 40. As the inner frame 40 is rotated, forces imparted onto the outer frame 42 cause the outer frame 42 to deform toward an elliptical shape, radially expanding into the commissures AC, PC and engaged radially for fixation and sealing as shown in FIG. 7. In some embodiments, a radial shape of the inner frame 40 remains constant during manipulation of the connection assembly 44A (referenced generally in FIG. 7).

The adjustable shape features of the outer frame 42 allow the clinician to "set" the level of interference between the prosthetic heart valve 30 and native anatomy in a manner that avoids impact on the LVOT (FIG. 1) and coronary sinus. The clinician can determine how much rotation is needed to get an appropriate fit between the native anatomy and the outer frame 42, thereby preventing LVOT obstruction, etc.

Figure 8:
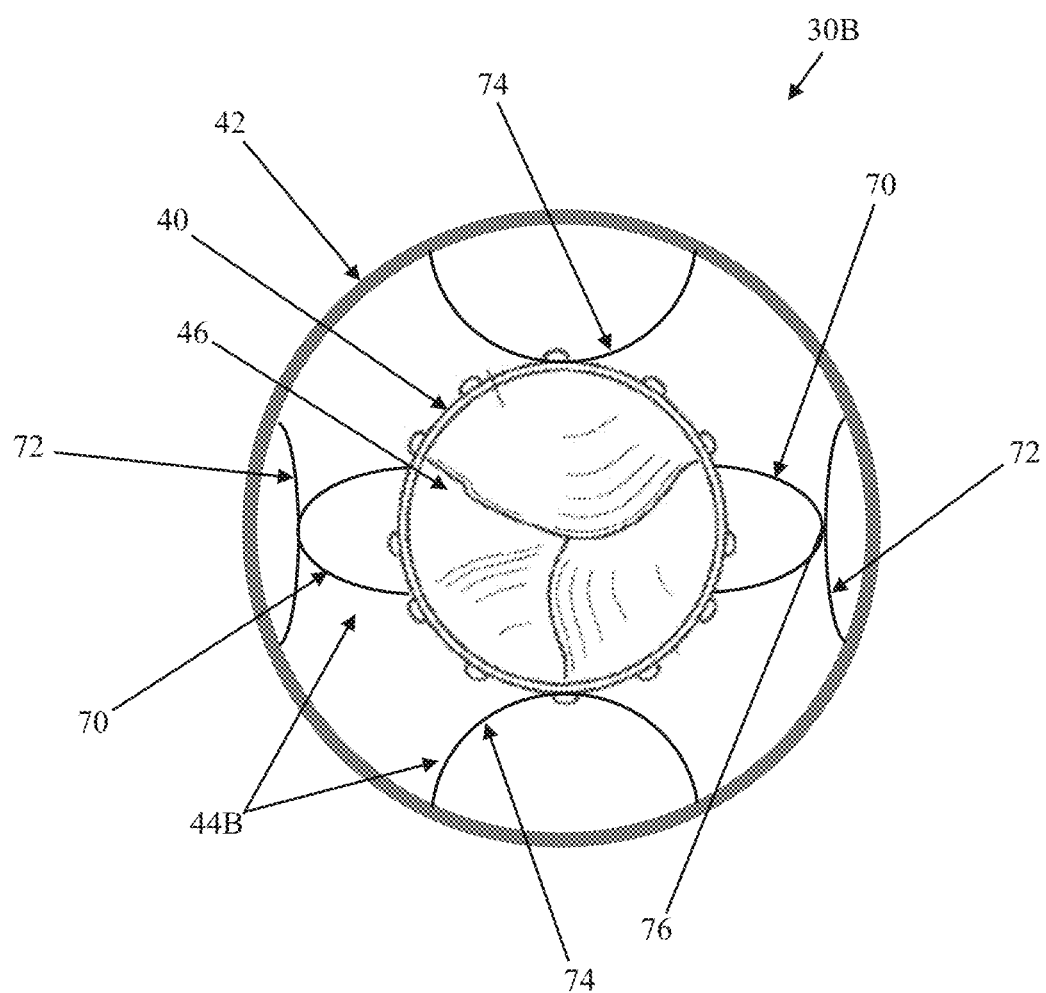
FIG. 8 is a simplified plan view of another prosthetic heart valve in accordance with principles of the present disclosure and in an initial deployed state.
Figure 9:
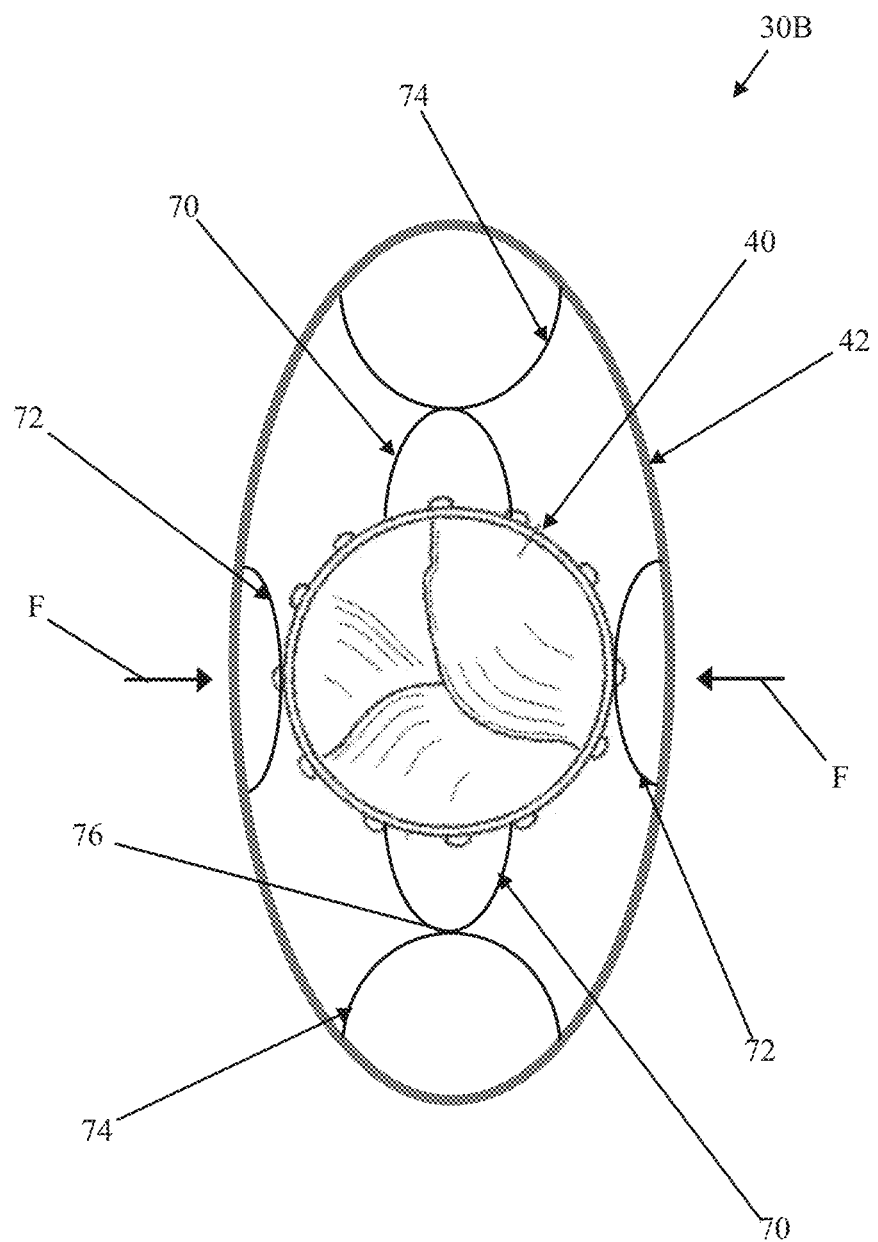
FIG. 9 is a simplified plan view of the prosthetic heart valve of FIG. 8 in a final deployed state.

Another prosthetic heart valve 30B in accordance with principles of the present disclosure is schematically illustrated in FIGS. 8 and 9. As a point of reference, FIG. 8 illustrates an initial deployed state of the prosthetic heart valve 30B, whereas FIG. 9 is one example of a final deployed state. The prosthetic heart valve 30B includes the inner frame 40, the outer frame 42, the valve structure 46, and the optional skirt as described above, along with a connection assembly 44B (referenced generally). The connection assembly 44B can be configured to permit rotation of the of inner frame 40 relative to the outer frame 42, and includes a plurality of connecting members, such as first connecting members 70, second connecting members 72, and third connecting members 74. The first connecting members 70 can be attached to and project outwardly from the inner frame 40, for example from opposite sides of the inner frame 40 as shown. The first connecting members 70 can each assume the lobe-like shape forming or defining an apex 76. The second connecting members 72 and the third connecting members 74 can be attached to and project inwardly from the outer frame 42. For example, two of the second connecting members 72 can be included and arranged opposite one another as shown; similarly, two of the third connecting members 74 can be included and arranged opposite one another. With this non-limiting construction, the second and third connecting members 72, 74 are alternately positioned along a circumference of the outer frame 42. Regardless, the second connecting members 72 and the third connecting members 74 can have a lobe-like shape, with at least one property of the second connecting members 72 differing from that of the third connecting members 74 (e.g., size, shape, stiffness, etc.) for reasons made clear below.

The connecting members 70, 72, 74 can be made from stainless steel, a pseudo-elastic metal such as a nickel titanium alloy or Nitinol™, or a so-called super alloy, which may have a base metal of nickel, cobalt, chromium, or other metal. In some embodiments, the connecting members 70, 72, 74 and corresponding connection with the inner and outer frames 40, 42, are configured to facilitate the transitioning between the compressed and normal (expanded) conditions as described above. For example, the connecting members 70, 72, 74 can have a self-expanding attribute, capable of returning to the initial deployed state or normal expanded condition of FIG. 8 from the compressed condition (e.g., such as when the prosthetic heart valve 30B is compressed and loaded within a delivery sheath or catheter).

In addition, physical properties of the connecting members 70, 72, 74 (e.g., size, shape, stiffness, etc.) are selected to provide the initial deployed state of FIG. 8, rotation of the inner frame 40 relative to outer frame 42, and the final deployed state of FIG. 9 following rotation of the inner frame 40. In the initial deployed state, the apex 76 of each of the first connecting members 70 bears against a corresponding one of the second connecting members 72, and the third connecting members 74 bear against the inner frame 40, with the corresponding physical properties resulting in the outer frame 42 being maintained substantially concentric (i.e., within 10% of a truly concentric relationship) about the inner frame 40. The lobe-like shapes of the connecting members 70, 72, 74 permits rotation of the inner frame 40 relative to the outer frame 42 (e.g., the inner frame 40 has been rotated in a clockwise direction in transitioning from the state of FIG. 8 to the state of FIG. 9). For example, a sliding interface is provided between the first connecting members 70 and the corresponding second connecting member 72 in the initial deployed state; thus, as a rotational or moment force is applied to the inner frame 40 while the outer frame 42 is maintained stationary (e.g., due to interference between the outer frame 42 and the native anatomy; represented by radial forces F in the FIG. 9), the first connecting members 70 are caused to slide off of or circumferentially away from the corresponding second connecting member 72. With continued rotation of the inner frame 40, the apex 76 of each of the first connecting members 70 is brought into contact with a corresponding one of the third connecting members 74. As the inner frame 40 is even further rotated, an interface between the first connecting members 70 and corresponding third connecting member 74, and optionally the radial forces F acting upon the outer frame 42, causes the outer frame 42 to deform toward an elliptical shape of the final deployed state as in FIG. 9. In the final deployed state, the apex 76 of each of the first connecting members 70 bears against a corresponding one of the third connecting members 74, whereas the second connecting members 72 may bear against the inner frame 40.

Delivery and deployment of the prosthetic heart valve 30B can be akin to the descriptions above with respect to the prosthetic heart valve 30A. For example, the prosthetic heart valve 30B is loaded to and compressed within a delivery device (not shown). The delivery device is then manipulated to deliver the prosthetic heart valve 30B, in the delivery state, to a target site (e.g., native heart valve). The delivery device is then operated to at least partially release the prosthetic heart valve 30B such that the prosthetic heart valve 30B transitions (expands) to the initial deployed state (FIG. 8). In the initial deployed state at the native heart valve anatomy (e.g., native mitral valve), the inner and outer frames 40, 42 are concentric and at least partially linked by the connection assembly 44B. The connection assembly 44B can then be adjusted by the clinician (e.g., the inner frame 40 rotated relative to the outer frame 42) to transition the prosthetic heart valve 30B to a final deployed state, varying the radial interference and the profile of the outer frame 42 to a shape more commensurate with the natural shape of the native valve annulus (e.g., elliptical shape as in FIG. 9) and conforms to the native anatomy. Once the prosthetic heart valve 30B is fully positioned, the level of radial force applied by the prosthetic heart valve 30B to anatomical features such as the LVOT (FIG. 1) can be evaluated and the inner frame 40 rotated to effectuate local forces as desired.

Figure 10:
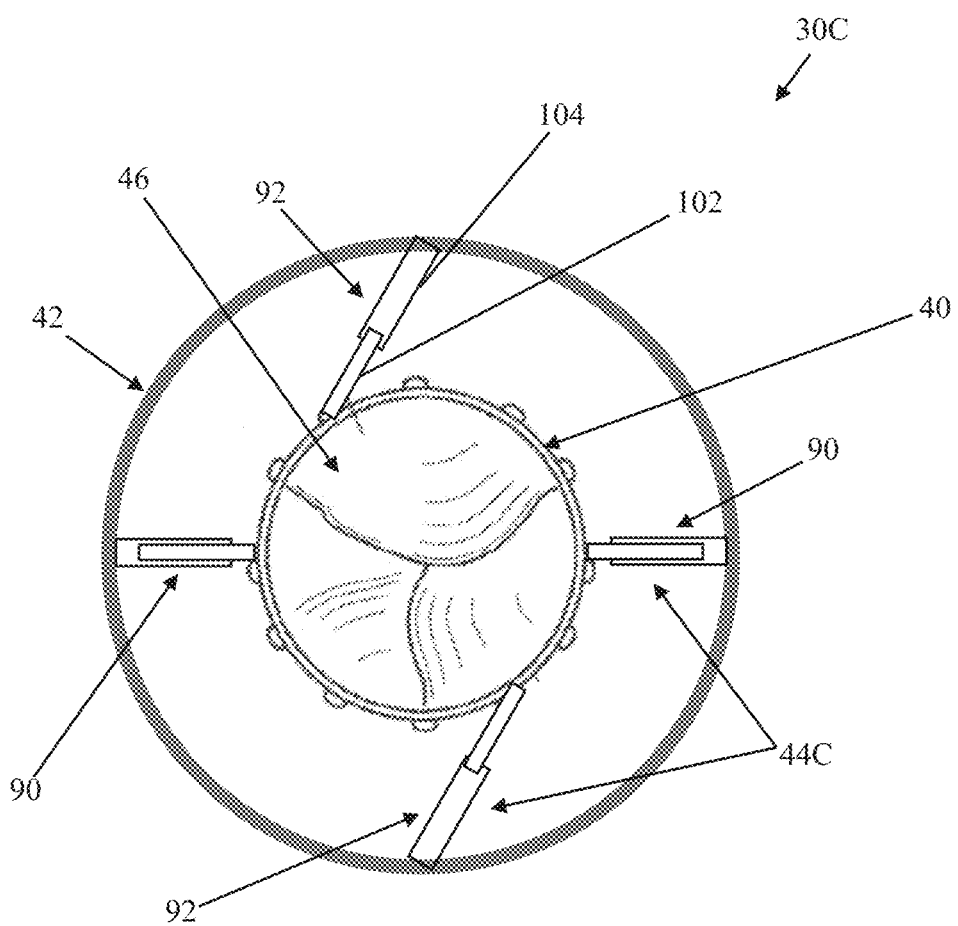
FIG. 10 is a simplified plan view of another prosthetic heart valve in accordance with principles of the present disclosure and in an initial deployed state.
Figure 11:
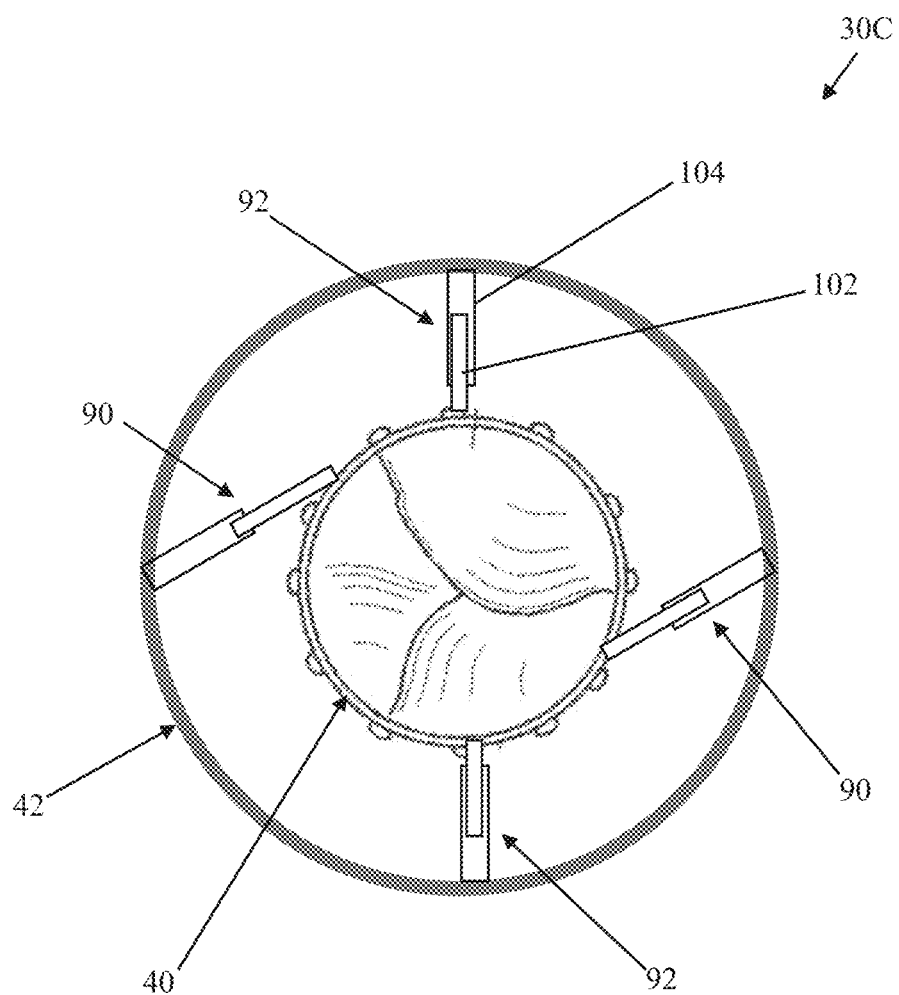
FIG. 11 is a simplified plan view of the prosthetic heart valve of FIG. 10 transitioning from the initial deployed state to a final deployed state.
Figure 12:
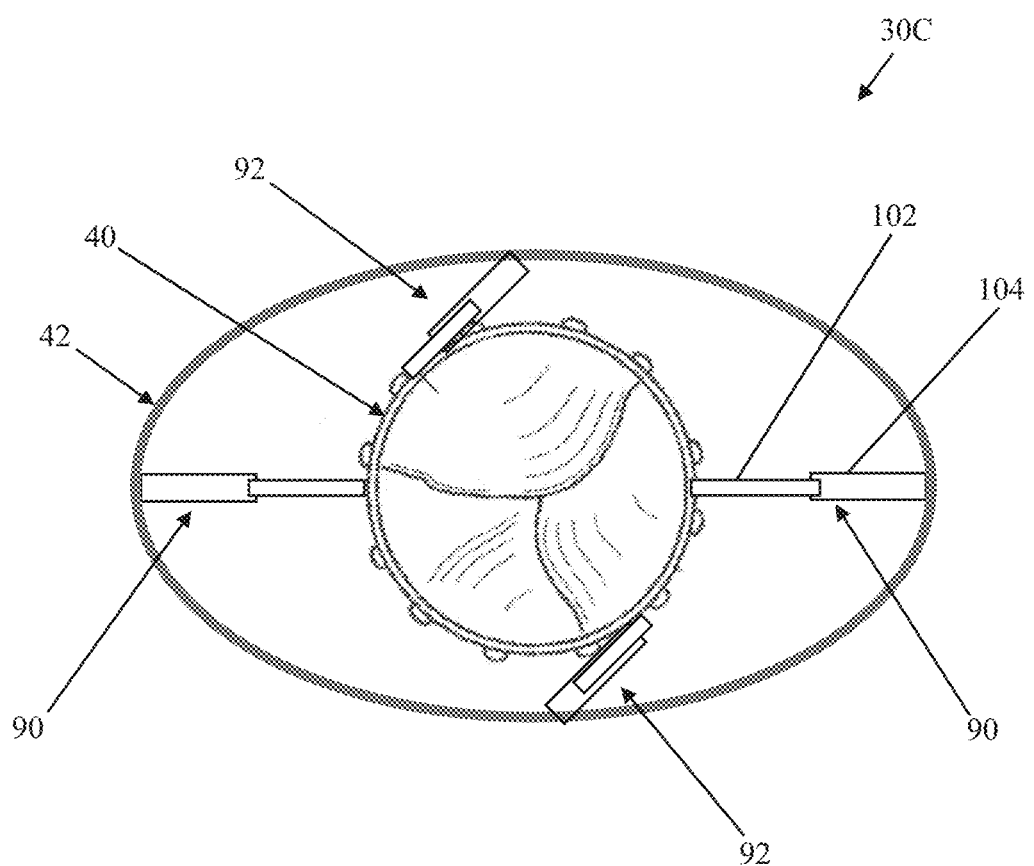
FIG. 12 is a simplified plan view of the prosthetic heart valve of FIG. 10 in a final deployed state.
Figure 21:
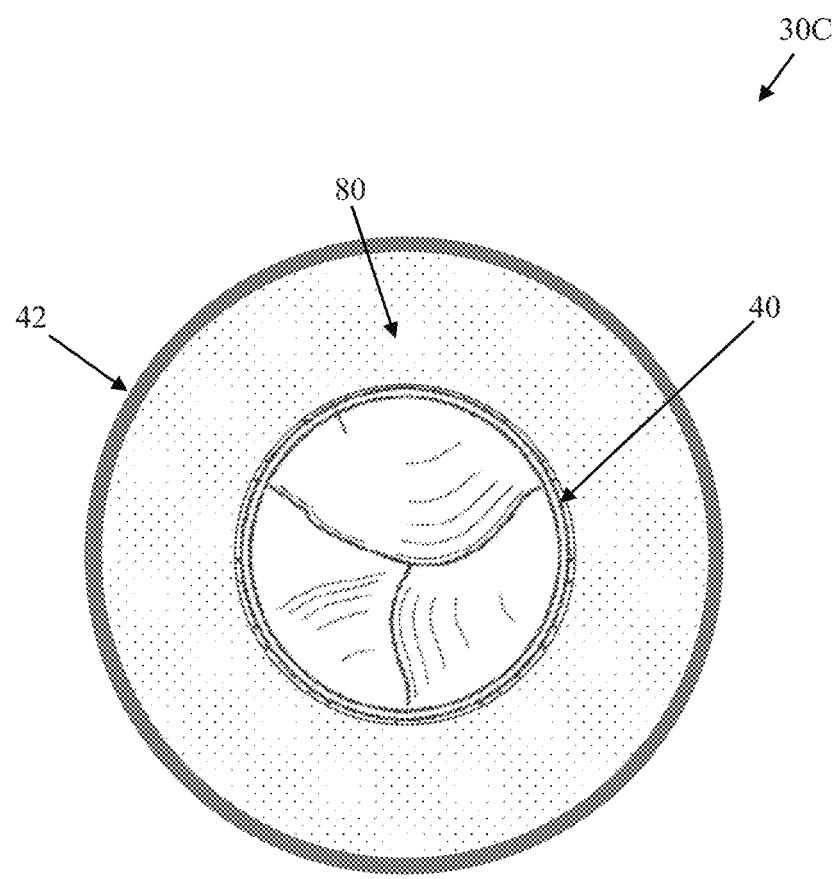
FIG. 21 is a simplified plan view of the prosthetic heart valve of FIG. 10 and further illustrating an optional skirt.

Another prosthetic heart valve 30C in accordance with principles of the present disclosure is schematically illustrated in FIGS. 10-12. As a point of reference, FIG. 10 illustrates an initial deployed state of the prosthetic heart valve 30C, whereas FIG. 12 is one example of a final deployed state. The prosthetic heart valve 30C includes the inner frame 40, the outer frame 42, the valve structure 46, and the optional skirt as described above (and as shown, for example, at 80 in FIG. 21), along with a connection assembly 44C (referenced generally). The connection assembly 44C can be configured to permit rotation of the inner frame 40 relative to the outer frame 42, and includes a plurality of arm pairs, such as first arm pairs 90 and second arm pairs 92. Each of the arm pairs 90, 92 includes a first arm 102 projecting from an exterior of the inner frame 40 and a second arm 104 projecting from an interior of the outer frame 42. The first and second arms 102, 104 of each arm pair 90, 92 interface with one another to dictate a radial spacing between the inner and outer frames 40, 42 at a location of the respective arm pair 90, 92, affording the clinician the ability to increase/decrease radial forces applied to the outer frame 42 and in turn, adjust a shape of the outer frame 42.

Figure 13A:
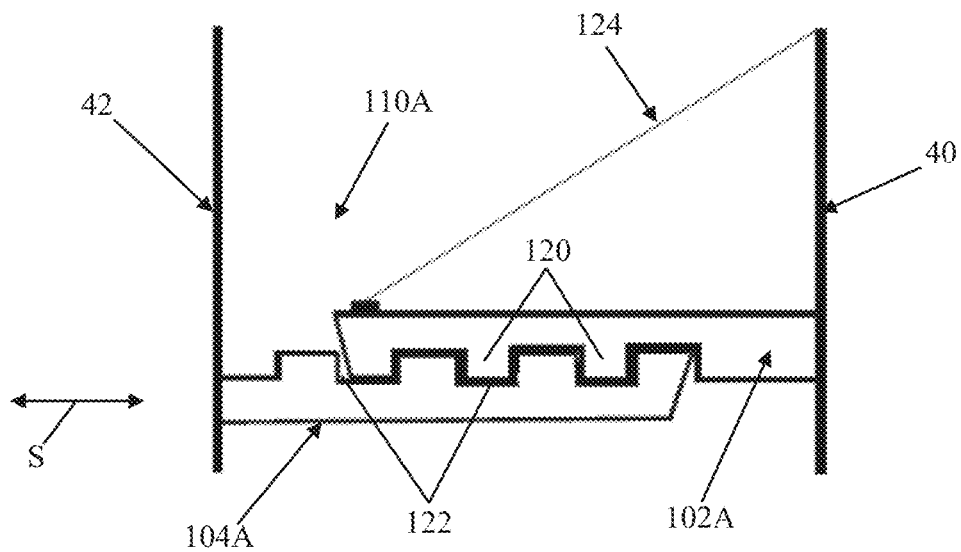
FIGS. 13A-13C are simplified side views of an arm pair useful with the prosthetic heart valves of the present disclosure.
Figure 13B:
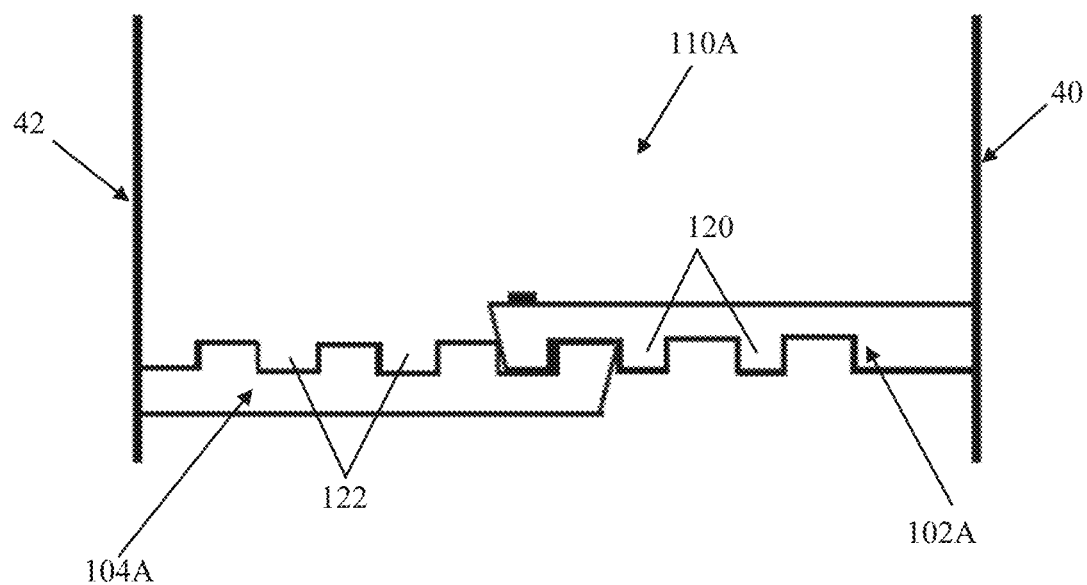
Figure 13C:
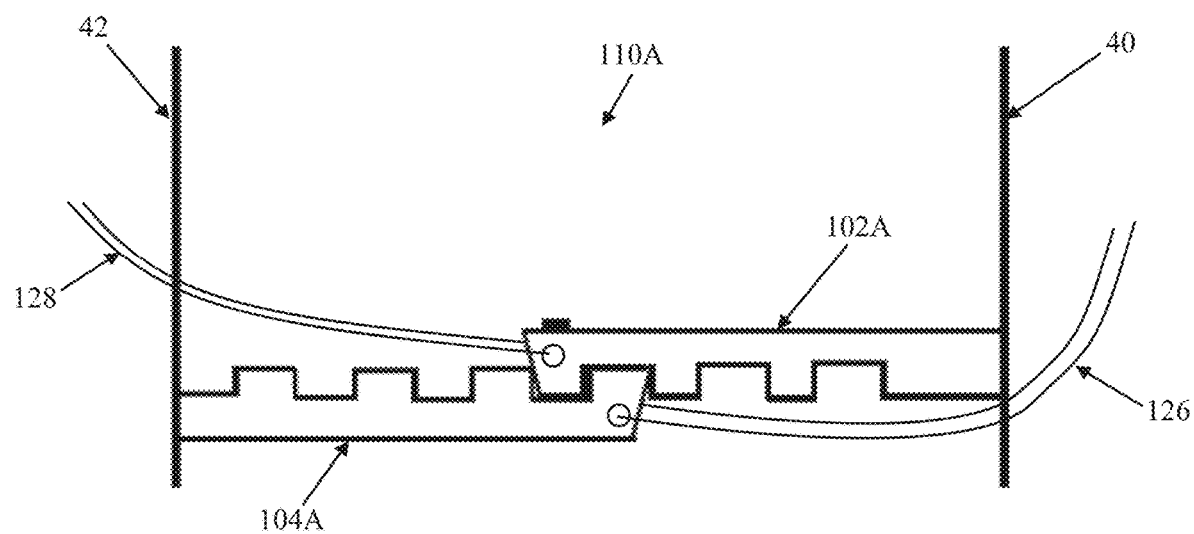

In some embodiments, the first arm 102 is slidably connected with the corresponding second arm 104 at each of the arm pairs 90, 92. In other embodiments, a rotatable connection is established between the corresponding first and second arms 102, 104. The first and second arms 102, 104 can incorporate complementary engagement features that selectively lock or otherwise provide selective control over a relationship of the arms 102, 104 relative to one another. For example, one embodiment of an arm pair 110A useful with any of the connection assemblies of the present disclosure (e.g., as one or more of the arm pairs 90, 92) is provided in FIGS. 13A and 13B. As shown, the arm pair 110A includes first and second arms 102A, 104A. The first arm 102A can include or form a plurality of teeth 120, whereas the second arm 104A forms or defines a plurality of slots 122 each sized and shaped to receive a corresponding one of the teeth 120. With this construction, the first arm 102A can slide relative to the second arm 104A in the direction of the arrow S; at various longitudinal positions of the first arm 102A relative to the second arm 104A, one or more of the teeth 120 will nest within a corresponding one of the slots 122, thereby impeding further movement of the arms 102A, 104A relative to one another. By forcibly sliding the first arm 102A relative to the second arm 104A, a corresponding distance between the inner and outer frames 40, 42 can be altered at a location of the arm pair 100A. The complementary engagement features operate to maintain the arms 102A, 104A at the selected position. FIG. 13A further reflects that in some embodiments, one or more tension members 124 can be provided with any of the connection assembly arm pairs of the present disclosure that is temporarily connected to the first arm 102A and/or the second arm 104A (e.g., as part of the transcatheter prosthetic heart valve delivery device). The tension member 124 can assume various forms, such as a rod, chord, line, suture, etc. By manipulating the tension member 124, a user can apply a force or tension onto the first arm 102A as part of a shape adjustment operation. The tension member(s) 124 can assume other forms conducive to user manipulation of the first arm 102A relative to the second arm 104A are also acceptable, for example a tension member temporarily attached to the second arm 104A and/or the inner frame 40. For example, FIG. 13C illustrates a first tension member 126 (in the form of a line or suture) connected to the first arm 102A, and a second tension member 128 (in the form of a line or suture) releasably connected to the second arm 104A. In other embodiments, only one of the first and second tension members 126, 128 is included. The first tension member 126 (where provided) is looped through the first arm 102A, and the second tension member 128 (where provided) is looped through the second arm 104A. Following deployment of the corresponding prosthetic heart valve, the tension members 126, 128 can be removed by pulling on one end thereof.

Figure 14A:
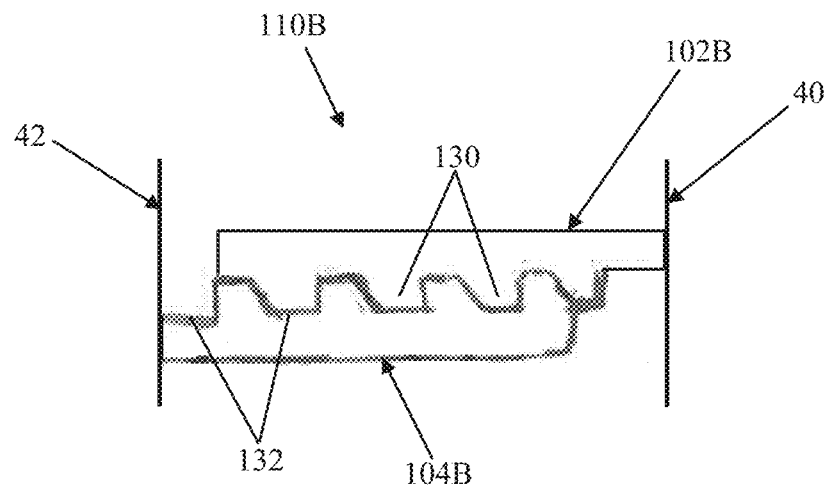
FIGS. 14A and 14B are simplified side views of another arm pair useful with the prosthetic heart valves of the present disclosure.
Figure 14B:
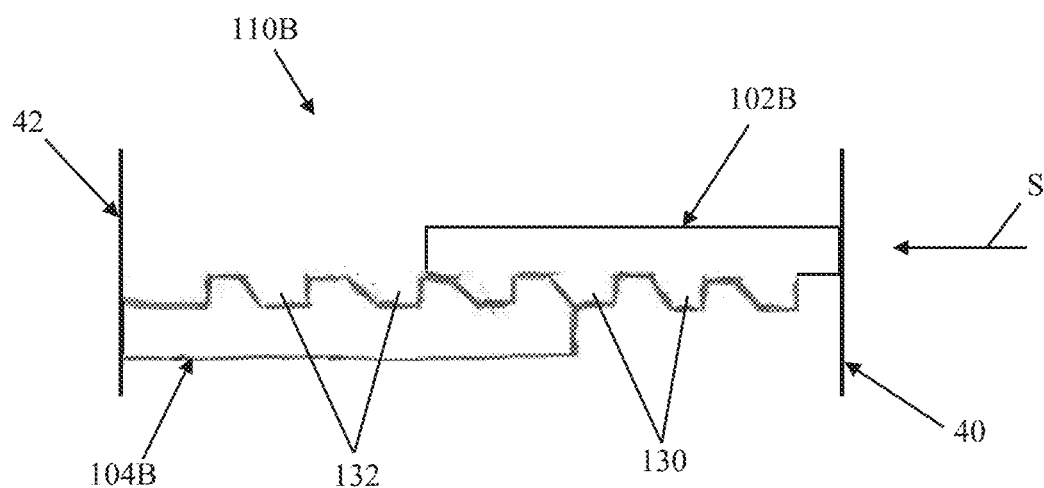

Returning to FIGS. 13A and 13B, in some embodiments, the arms 102A, 104A can have a generally identical configuration, with the shape of the teeth 120 matching a shape of the slots 122, for example a symmetrical shape as shown with an angled leading edge as shown. In other embodiments, the teeth 120 (and/or the slots 122) can have a shape that promotes the teeth 120 more readily disengaging from the slots 122 in one direction and resists disengagement in the opposite direction. This directional bias can also be incorporated into the second arm 104B (and in particular a shape of the walls at opposite ends of each of the slots 122). Other shapes are also envisioned (e.g., each of the teeth 120 can have a more asymmetric shape). For example, another embodiment of an arm pair 110B useful with any of the connection assemblies of the present disclosure is shown in FIGS. 14A and 14B. The arm pair 110B includes first and second arms 102B, 104B. The first arm 102B can include or form a plurality of teeth 130, whereas the second arm 104B forms or defines a plurality of slots 132 each sized and shaped to receive a corresponding one of the teeth 130. The complementary shape of the teeth 130 and slots 13102 is asymmetrical or biased in a direction of the outer frame 42 such that the first and second arms 102B, 104B are more easily caused or tensioned toward one another (i.e., drawing the inner and outer frames 40, 42 closer to one another). Thus, in some embodiments, the arm pair 110B can be appropriate for lessening a spacing between the inner and outer frames 40, 42 when transitioning the corresponding prosthetic heart valve from the initial deployed state to the final deployed state (i.e., FIG. 14B reflects a possible initial deployed state, and FIG. 14A reflects a possible final deployed state, with the first arm 102B sliding relative to the second arm 104B in the direction of the arrow S). At various longitudinal positions of the first arm 102B relative to the second arm 104B, one or more of the teeth 130 will nest within a corresponding one of the slots 132, thereby impeding further movement of the arms 102B, 104B relative to one another.

Figure 15A:
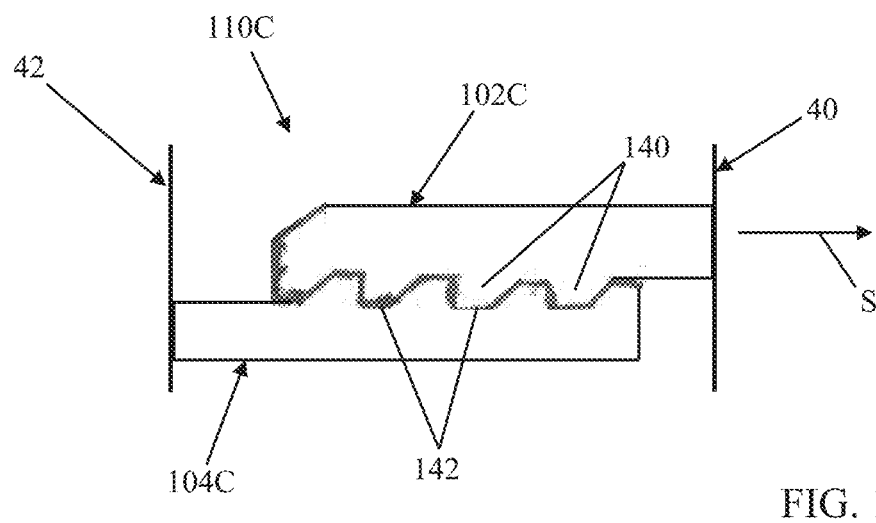
FIGS. 15A and 15B are simplified side views of another arm pair useful with the prosthetic heart valves of the present disclosure.
Figure 15B:
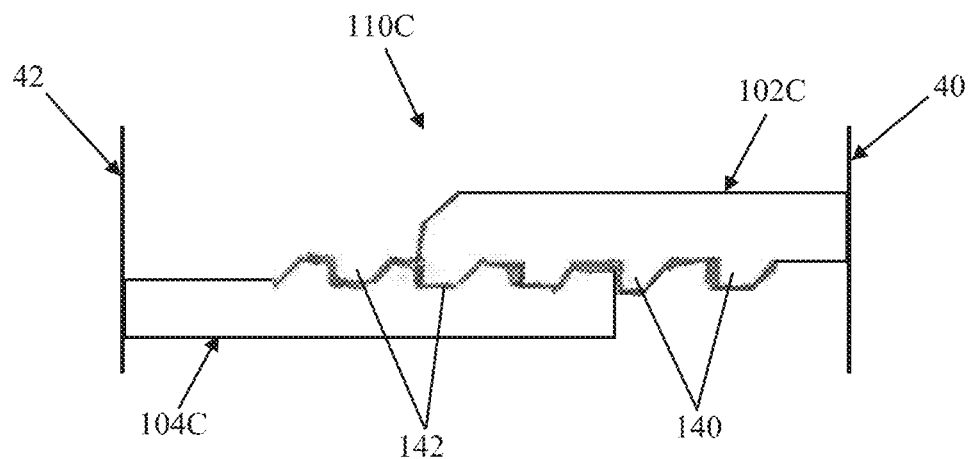

Another embodiment of an arm pair 110C useful with any of the connection assemblies of the present disclosure is shown in FIGS. 15A and 15B. The arm pair 110C includes first and second arms 102C, 104C. The first arm 102C can include or form a plurality of teeth 140, whereas the second arm 104C forms or defines a plurality of slots 142 each sized and shaped to receive a corresponding one of the teeth 140. The complementary shape of the teeth 140 and slots 142 is asymmetrical or biased in a direction of the inner frame 40 such that the first and second arms 102C, 104C are more easily caused or tensioned away from one another (i.e., forcing the inner and outer frames 40, 42 away from one another). Thus, in some embodiments, the arm pair 110C can be appropriate for increasing a spacing between the inner and outer frames 40, 42 when transitioning the corresponding prosthetic heart valve from the initial deployed state to the final deployed state (i.e., FIG. 15A reflects a possible initial deployed state, and FIG. 15B reflects a possible final deployed state, with the first arm 102C sliding relative to the second arm 104C in the direction of the arrow S). At various longitudinal positions of the first arm 102C relative to the second arm 104C, one or more of the teeth 140 will nest within a corresponding one of the slots 142, thereby impeding further movement of the arms 102C, 104C relative to one another.

Figure 16:
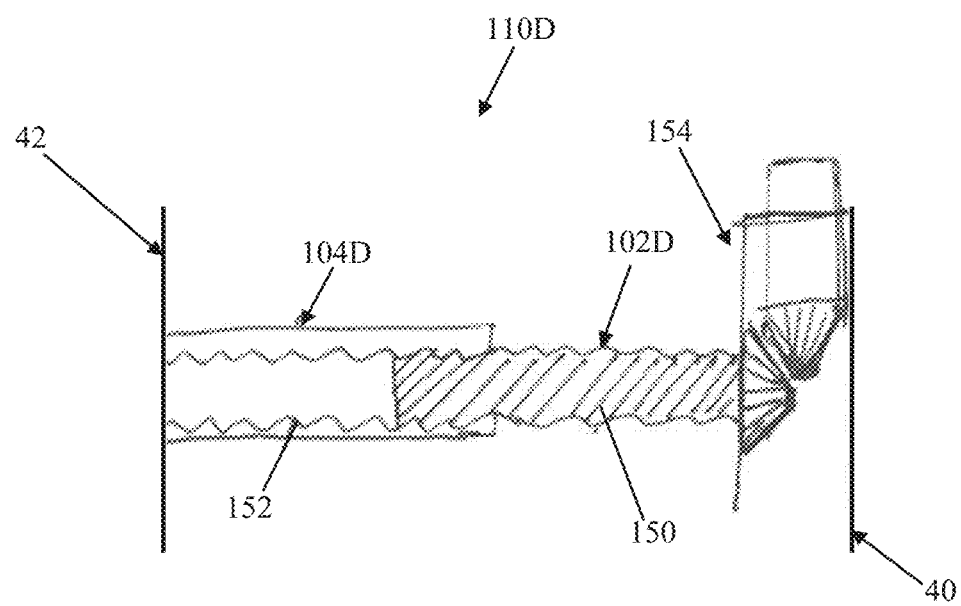
FIG. 16 is a simplified side view of another arm pair useful with the prosthetic heart valves of the present disclosure.

Another embodiment of an arm pair 110D useful with any of the connection assemblies of the present disclosure is shown in FIG. 16. The arm pair 110D includes first and second arms 102D, 104D. The first arm 102D can include or form external threads 150, whereas the second arm 104D forms or defines internal threads 152. The external and internal threads 150, 152 have complementary constructions such that the first arm 102D is threadably connected to the second arm 104D. In some embodiments, rotation of the first arm 102D relative to the second arm 104D will increase or decrease a longitudinal length of the arm pair 110D (and thus a spacing between the inner and outer frames 40, 42). For example, in some embodiments, rotation of the first arm 102D clockwise relative to the second arm 104D will decrease the length of the arm pair 110D, whereas counterclockwise rotation of the first arm 102D relative to the second arm 104D will increase the length of the arm pair 110D. In alternative embodiments, the external thread 150 is formed by the second arm 104D, and the complementary internal thread 152 is provided with the first arm 102D. In some embodiments, one or more gear boxes 154 (e.g., a 90 degree gear box as shown in FIG. 16) are provided to facilitate user application of a rotational force onto, or a change the rotational direction of, the arm 102D, 104D that comprises the external threads 150 to be manipulated or rotated. The one or more gear boxes can be incorporated, coupled or attached to the inner frame 40 and/or the outer frame 42. In some embodiments, the inner frame 40 comprises one or more gear boxes coupled to one or more arm pairs 110D. In other embodiments, the outer frame 42 comprises one or more gear boxes couple to one or more arm pairs 110D.

Returning to FIGS. 10-12, the arm pairs 90, 92 can assume a wide variety of forms as described above, including, for example, the non-limiting arm pair formats 110A (FIG. 13A), 110B (FIG. 14A), 110C (FIG. 15A), 110D (FIG. 16). In the initial deployed state, a length of each of the first arm pairs 90 is less than a length of each of the second arm pairs 92. With this mind, the first arm pairs 90 can each have a construction akin to the arm pair 110C of FIGS. 15A and 15B, generally configured to increase in length when the inner frame 40 is rotated relative to the outer frame 42 (e.g., approximately one quarter turn clockwise as shown in FIG. 11), and the second arm pairs 92 can each have a construction akin to the arm pair 110B of FIGS. 14A and 14B, generally configured to decrease in length with the inner frame 40 is rotated relative to the outer frame 42. Following clockwise rotation of the inner frame 40 relative to the outer frame 42 (e.g., transitioning from the arrangement of FIG. 10 to the arrangement of FIG. 11), the inner frame 40 is then rotated in an opposite direction (e.g., counterclockwise) relative to the outer frame 42, for example about a quarter turn as shown in FIG. 12. Because the first arm pairs 90 increased in length following the clockwise rotation of the inner frame 40 and are configured to overtly resist compressive forces (e.g., will not decrease in length), the first arm pairs 90 will push the outer frame 42 radially outwardly away from the inner frame 40 with the subsequent counterclockwise rotation of the inner frame 40 so that the distance between the inner and outer frames 40, 42 adjacent or near each of the first arm pairs 90 is increased as reflected by FIG. 12. And because the second arm pairs 92 decreased in length following the clockwise rotation of the inner frame 40 and are configured to overtly resist expansive forces (e.g., will not increase in length), the second arm pairs 92 will pull the outer frame 42 radially inwardly toward the inner frame 40 with the subsequent counterclockwise rotation of the inner frame 40 so that the distance between the inner and outer frames 40, 42 adjacent or near each of the second arm pairs 92 is decreased as reflected by FIG. 12. Thus, clockwise rotation of the inner frame 40 relative to the outer frame 42 from the initial deployed state followed by a similar amount of counterclockwise rotation of the inner frame 40 relative to the outer frame 42 will transition the outer frame 42 from a circular-like shape in the initial deployed state (FIG. 10) to an elliptical-like shape in the final deployed state (FIG. 12).

If desired, in some embodiments, the amount or level of ellipticity created in the outer frame 42 can be a function of the number of times and/or the degree of rotation the inner frame 40 is rotated clockwise and then counterclockwise relative to the outer frame 42. For example, if the first combination of a clockwise/counterclockwise rotation of the inner frame 40 relative to the outer frame 42 does not create the desired ellipticity in the outer frame 42, and second or third combination of clockwise/counterclockwise rotation of the inner frame 40 relative to the outer frame 42 can be performed, thereby creating more ellipticity in the outer frame 42. In some embodiments, multiple combinations of clockwise and counterclockwise rotation of the inner frame 40 relative to the outer frame 42 can be performed to transition the outer frame 42 from a circular-like shape to a desired noncircular-like shape (e.g., an elliptical shape).

In alternative embodiments, there may be more than or less than four of the arm pairs 90, 92 connecting the inner frame 40 to the outer frame 42. In alternative embodiments, in an initial deployed state of the prosthetic heart valve 30C, there may be arm pairs of more than two different lengths connected in the inner frame 40 to the outer frame 42. In alternative embodiments, one or more of the arm pairs provided with the connection assembly 44C can be configured to decrease the distance between the inner frame 40 and the outer frame 42 upon transitioning the prosthetic heart valve 30C from an initial deployed state to a final deployed state. In alternative embodiments, one or more of the arm pairs provided with the connection assembly 44C can be configured to increase the distance between the inner frame 40 and the outer frame 42 upon transitioning the prosthetic heart valve 30C from an initial deployed state to a final deployed state.

In some embodiments, one or more of the arm pairs 90, 92 are rigid, semi-rigid, semi-flexible, and/or flexible. In some embodiments, one or more portions of one or more of the first arms 102 and/or the second arms 104 are rigid, semi-rigid, semi-flexible, and/or flexible.

In some embodiments, the connection assembly 44C can include one or more components in addition to the arm pairs 90, 92. For example, locking structures or mechanisms can be provided that selectively lock or unlock the inner frame 40 relative to the outer frame 42 at various rotational positions.

Delivery and deployment of the prosthetic heart valve 30C can be akin to the descriptions above with respect to the prosthetic heart valve 30A. For example, the prosthetic heart valve 30C is loaded to and compressed within a delivery device (not shown). The delivery device is then manipulated to deliver the prosthetic heart valve 30C, in the delivery state, to a target site (e.g., native heart valve). The delivery device is then operated to at least partially release the prosthetic heart valve 30C such that the prosthetic heart valve 30C transitions (expands) to an initial deployed state. In the initial deployed state at the native heart valve anatomy (e.g., native mitral valve), the inner and outer frames 40, 42 are concentric and linked by the arm pairs 90, 92. The connection assembly 44C can then be adjusted by the clinician (e.g., the inner frame 40 rotated relative to the outer frame 42) to transition the prosthetic heart valve 30C to a final deployed state as described above, varying the radial interference and the profile of the outer frame 42 to a shape more commensurate with the natural shape of the native valve annulus (e.g., elliptical shape as in FIG. 12) and conforms to the native anatomy. Once the prosthetic heart valve 30C is fully positioned, the level of radial force applied by the prosthetic heart valve 30C to anatomical features such as the LVOT (FIG. 1) can be evaluated and the inner frame 40 rotated to effectuate local forces as desired.

Figure 17:
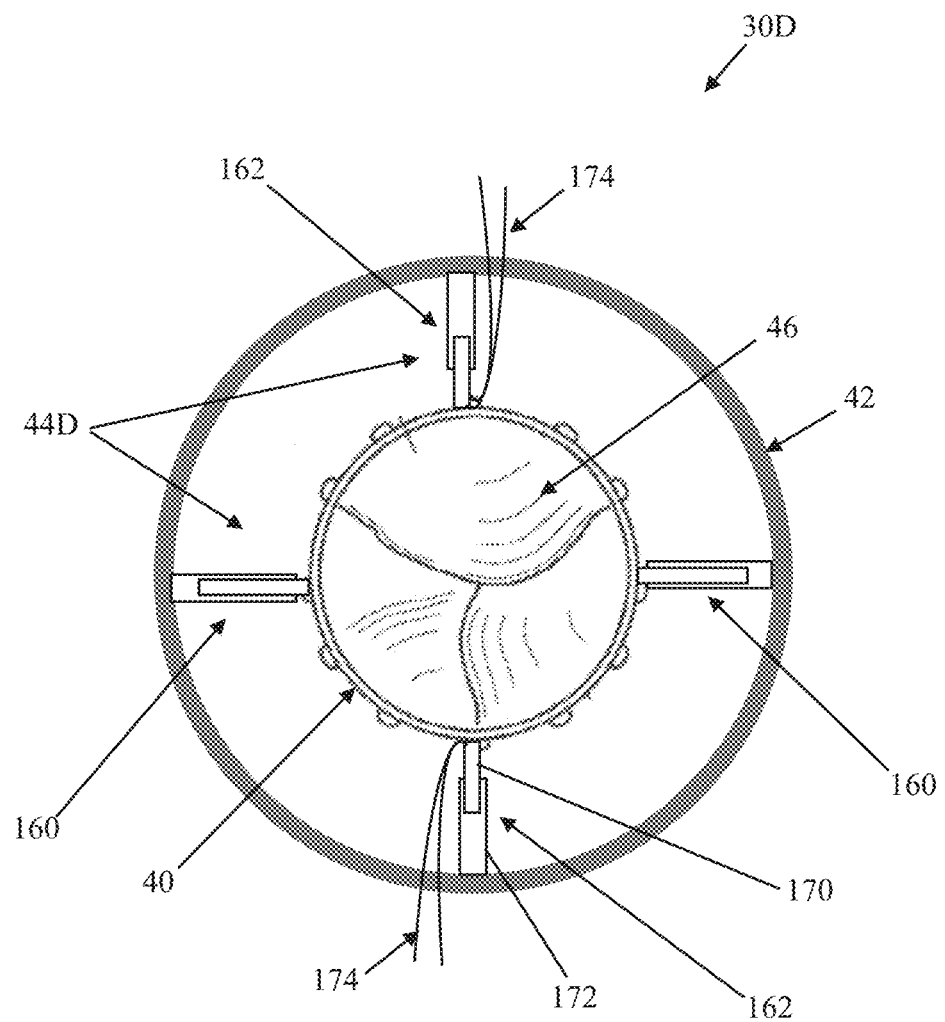
FIG. 17 is a simplified plan view of another prosthetic heart valve in accordance with principles of the present disclosure and in an initial deployed state.
Figure 18:
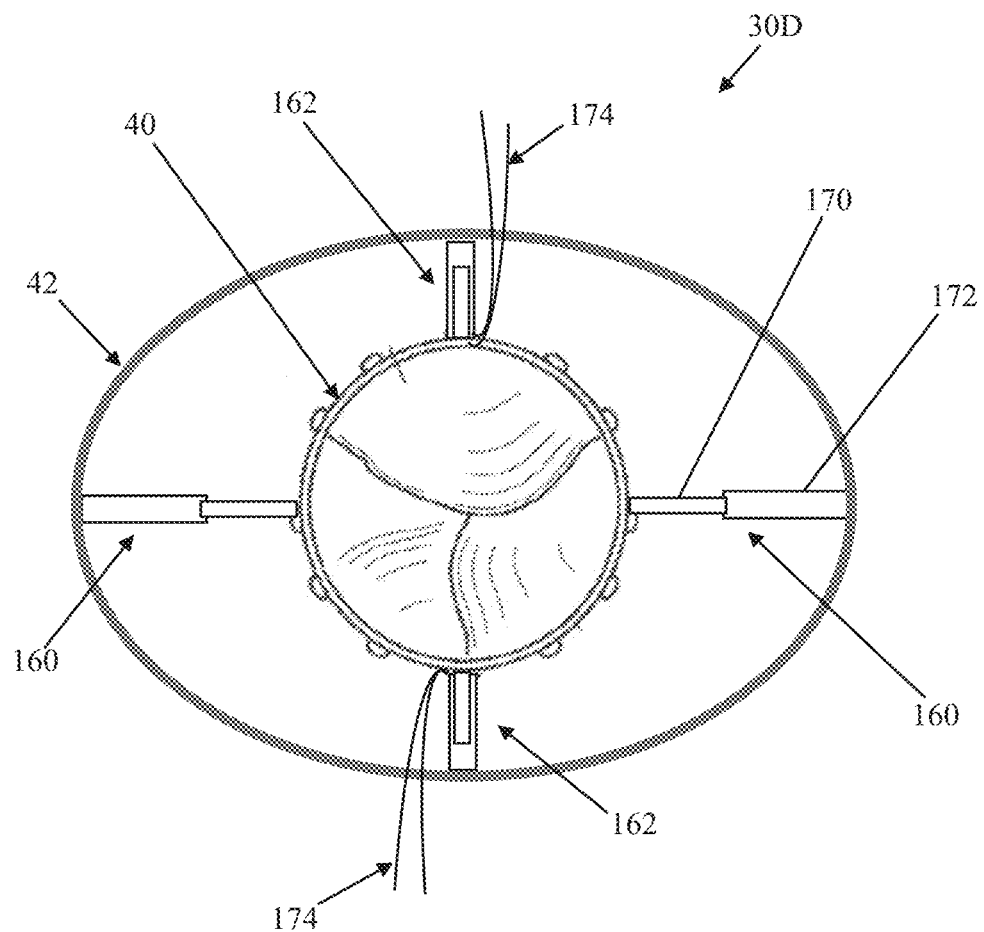
FIG. 18 is a simplified plan view of the prosthetic heart valve of FIG. 17 in a final deployed state.

The prosthetic heart valves and corresponding connection assemblies of the present disclosure can alternatively be configured to facilitate transitioning between the initial deployed state and a final deployed state without rotation of the inner frame 40 relative to the outer frame 42. For example, another prosthetic heart valve 30D in accordance with principles of the present disclosure is schematically illustrated in FIGS. 17 and 18. As a point of reference, FIG. 17 illustrates an initial deployed state of the prosthetic heart valve 30D, whereas FIG. 18 is one example of a final deployed state. The prosthetic heart valve 30D includes the inner frame 40, the outer frame 42, the valve structure 46, and the optional skirt as described above, along with a connection assembly 44D (referenced generally). The connection assembly 44D is configured to not require or permit rotation of the inner frame 40 relative to the outer frame 42, and includes a plurality of arm pairs, such as first arm pairs 160 and second arm pairs 162. Each of the arm pairs 160, 162 includes a first arm 170 projecting from an exterior of the inner frame 40 and a second arm 172 projecting from an interior of the outer frame 42. The first and second arms 170, 172 of each arm pair 160, 162 interface with one another to dictate a radial spacing between the inner and outer frames 40, 42 at a location of the respective arm pair 160, 162, affording the clinician the ability to increase/decrease radial forces applied to the outer frame 42 and in turn, adjust a shape of the outer frame 42.

The arm pairs 160, 162 can assume a wide variety of forms as described above, including, for example, the non-limiting arm pair formats 110A (FIG. 13A), 110B (FIG. 14A), 110C (FIG. 15A), 110D (FIG. 16). In the initial deployed state (FIG. 17), a length of each of the first arm pairs 160 is the same as the length of each of the second arm pairs 162 to promote or maintain the circular-like shape of the outer frame 42 and the substantially concentric arrangement of the outer frame 42 relative to the inner frame 40. In some embodiments, to facilitate transition from the initial deployed state to the final deployed state of FIG. 18, the first arm pairs 160 are each generally configured to be more readily increased in length and resist compression, whereas the second arm pairs 162 are each generally configured to be more readily decreased in length and resist expansion. With this mind, the first arm pairs 160 can each have a construction akin to the arm pair 110C of FIGS. 15A and 15B, generally configured to be readily increased in length, and the second arm pairs 162 can each have a construction akin to the arm pair 110B of FIGS. 14A and 14B, generally configured to be readily decreased in length. In some embodiments, and as reflected by FIGS. 17 and 18, one or more tensioning members 174 can be provided with one or more of the arm pairs 160, 162 as described above. To transition the prosthetic heart valve 30D from the initial deployed state to the final deployed state, the tensioning members 174 of the second arm pairs 162 can be manipulated, pulled or tensioned by a delivery device and/or clinician to decrease the length of the second arm pairs 162.

In some embodiments, decreasing the length of the second arm pairs 162 will pull the outer frame 42 radially inward or toward the inner frame 40 so that the distance between the inner and outer frames 40, 42 adjacent or near the second arm pairs 162 will decrease. Applying an inward force or tension on opposite sides of the outer frame 42 at or near the second arm pairs 162 will cause the outer frame 42 to bulge radially outwardly at or near the first arm pairs 160. This radial outward movement of portions of the outer frame 42 at or near the first arm pairs 160 will cause the first arm pairs 160 to increase in length, thereby transitioning the outer frame 42 from the circular-like shape of the initial deployed state to an elliptical-like shape in the final deployed state of FIG. 18. The amount of ellipticity created in the outer frame 42 can be controlled by the tension applied on the tension members 174. Following deployment of the prosthetic heart valve 30D, the tensioning members 174 can be removed by pulling on one end. In other embodiments, the connection assembly 44D can be caused to transition from the initial deployed state to the final deployed state in a variety of other fashions. In alternative embodiments, there may be more or less than four of the arm pairs 160, 162 connecting the inner frame 40 to the outer frame 42.

Delivery and deployment of the prosthetic heart valve 30D can be akin to the descriptions above with respect to the prosthetic heart valve 30A. For example, the prosthetic heart valve 30D is loaded to and compressed within a delivery device (not shown). The delivery device is then manipulated to deliver the prosthetic heart valve 30D, in the delivery state, to a target site (e.g., native heart valve). The delivery device is then operated to at least partially release the prosthetic heart valve 30D such that the prosthetic heart valve 30D transitions (expands) to an initial deployed state. In the initial deployed state at the native heart valve anatomy (e.g., native mitral valve), the inner and outer frames 40, 42 are concentric and linked by the arm pairs 160, 162. The connection assembly 44D can then be adjusted by the clinician to transition the prosthetic heart valve 30D to the final deployed state as described above, varying the radial interference and the profile of the outer frame 42 to a shape more commensurate with the natural shape of the native valve annulus (e.g., elliptical shape as in FIG. 18) and conforms to the native anatomy. For example, the delivery device can be operated to transition the prosthetic heart valve 30D to the final deployed state. In some embodiments, the delivery device is configured to manipulate the connection assembly 44D by applying tension onto the tension members 174. Regardless, once the prosthetic heart valve 30D is fully positioned, the level of radial force applied by the prosthetic heart valve 30D to anatomical features such as the LVOT (FIG. 1) can be evaluated and the inner frame 40 rotated to effectuate local forces as desired.

Figure 19:
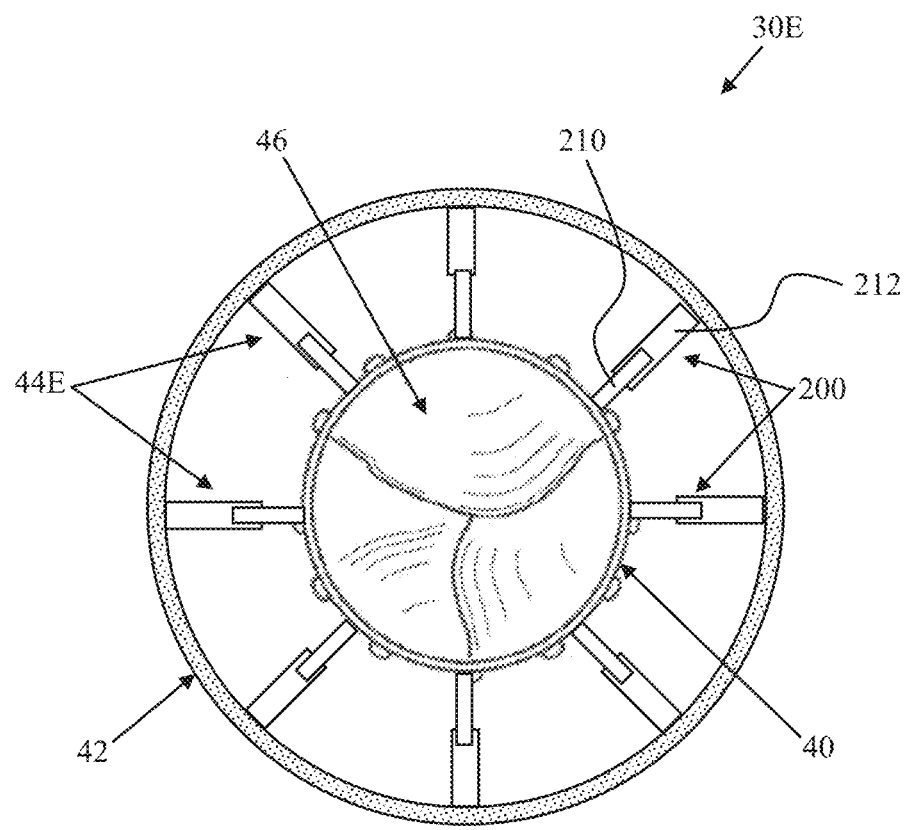
FIG. 19 is a simplified plan view of another prosthetic heart valve in accordance with principles of the present disclosure and in an initial deployed state
Figure 20:
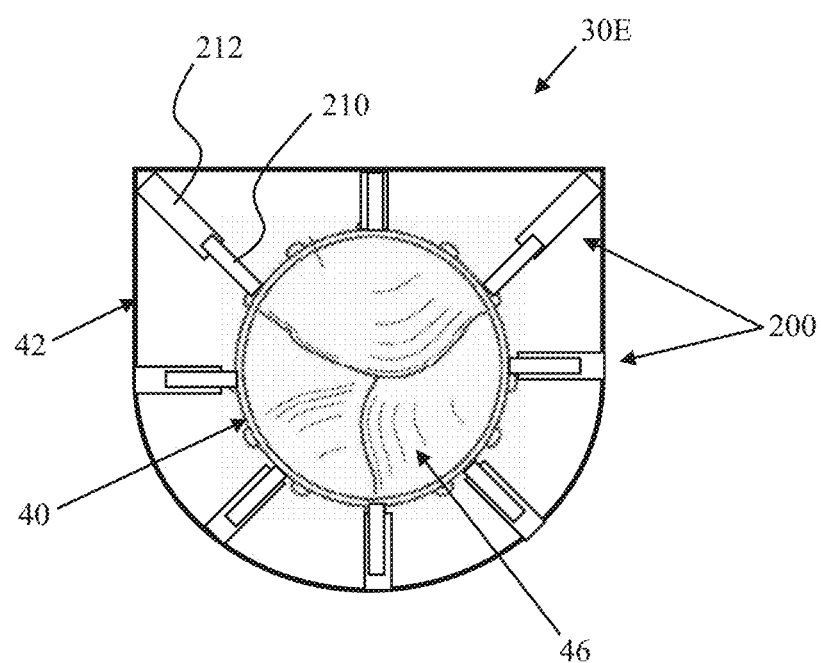
FIG. 20 is a simplified plan view of the prosthetic heart valve of FIG. 19 in a final deployed state.

Another prosthetic heart valve 30E in accordance with principles of the present disclosure is schematically illustrated in FIGS. 19 and 20. As a point of reference, FIG. 19 illustrates an initial deployed state of the prosthetic heart valve 30E, whereas FIG. 20 is one example of a final deployed state. The prosthetic heart valve 30E includes the inner frame 40, the outer frame 42, the valve structure 46, and the optional skirt as described above, along with a connection assembly 44E (referenced generally). The connection assembly 44E is configured to not require or permit rotation of the inner frame 40 relative to the outer frame 42, and includes a plurality of arm pairs 200. Each of the arm pairs 200 includes a first arm 210 projecting from an exterior of the inner frame 40 and a second arm 212 projecting from an interior of the outer frame 42. The first and second arms 210, 212 of each arm pair 200 interface with one another to dictate a radial spacing between the inner and outer frames 40, 42 at a location of the respective arm pair 200, affording the clinician the ability to increase/decrease radial forces applied to the outer frame 42 and in turn, adjust a shape of the outer frame 42.

The arm pairs 200 can assume a wide variety of forms as described above, including, for example, the non-limiting arm pair formats 110A (FIG. 13A), 110B (FIG. 14A), 110C (FIG. 15A), 110D (FIG. 16). In the initial deployed state (FIG. 19), a length of each of the pairs 200 is the same to promote or maintain the circular-like shape of the outer frame 42 and the substantially concentric arrangement of the outer frame 42 relative to the inner frame 40. In some embodiments, to facilitate transition from the initial deployed state to the final deployed state of FIG. 20, each of the arm pairs 200 are each generally configured to be increased or decreased in length; in other embodiments, selected ones of the arm pairs 200 are configured to be more readily increased in length and resist compression, whereas other ones of the arm pairs 200 are configured to be more readily decreased in length and resist expansion. With this in mind, some or all of the arm pairs 200 may have a construction akin to the arm pair 110D. To transition the prosthetic heart valve 30D from the initial deployed state (FIG. 19) to the final deployed state (FIG. 20), each arm pair 200 can be manipulated to change its length.

In some embodiments, decreasing the length of a selected one of the arm pairs 200 will pull the outer frame 42 radially inward or toward the inner frame 40 so that the distance between the inner and outer frames 40, 42 adjacent or near the selected arm pair 200 will decrease. Increasing the length of a selected one of the arm pairs 200 will push the outer frame 42 radially outward away from the inner frame 40 so that the distance between the inner and outer frames 40, 42 adjacent the selected arm pair 200 will increase. The amount that the outer frame 42 changes shape from the initial deployed state to a selected final deployed state is related to the amount each arm pair 200 is manipulated to increase or decrease in length. In alternative embodiments, there may be more or less than eight of the arm pairs 200 connecting the inner frame 40 to the outer frame 42. In some embodiments, the connection assembly 44E can include one or more different types or formats of the arm pairs 200 as described above. Depending on the desired final deployed state, the connection assembly 44E can include one or more combinations of differently formatted arm pairs 200. Different types of the arm pairs 200 can be used to manipulate different portions of the outer frame 42 into a desired final deployed state or shape.

Delivery and deployment of the prosthetic heart valve 30E can be akin to the descriptions above with respect to the prosthetic heart valve 30A. For example, the prosthetic heart valve 30E is loaded to and compressed within a delivery device (not shown). The delivery device is then manipulated to deliver the prosthetic heart valve 30E, in the delivery state, to a target site (e.g., native heart valve). The delivery device is then operated to at least partially release the prosthetic heart valve 30E such that the prosthetic heart valve 30E transitions (expands) to an initial deployed state. In the initial deployed state at the native heart valve anatomy (e.g., native mitral valve), the inner and outer frames 40, 42 are concentric and linked by the arm pairs 200. The connection assembly 44E can then be adjusted by the clinician to transition the prosthetic heart valve 30E to the final deployed state as described above, varying the radial interference and the profile of the outer frame 42 (e.g., the arm pairs 200 can each be adjusted) to a shape commensurate with the natural shape of the native valve annulus (e.g., D shape as in FIG. 20, for example when implanted at a native mitral valve annulus) and better conforming to the native anatomy. Once the prosthetic heart valve 30E is fully positioned, the level of radial force applied by the prosthetic heart valve 30E to anatomical features such as the LVOT (FIG. 1) can be evaluated and one or more of the arm pairs 200 adjusted to effectuate local forces as desired.

In some embodiments, the connection assembly provided with the prosthetic heart valves of the present disclosure can comprise various combinations of features of the connection assemblies 44A-44E described above. For example, the connection assembly can include one or more of the connecting members 50, 52 (FIG. 4), one or more of the connecting members 70, 72, 74 (FIG. 8), one or more of the arm pairs 90, 92 (FIG. 10), one or more of the arm pairs 110A (FIG. 13A), one or more of the arm pairs 110B (FIG. 14A), one or more of the arm pairs 110C (FIG. 15A), one or more of the arm pairs 110D (FIG. 16), one or more of the arm pairs 160, 162 (FIG. 17) and/or one or more of the arm pairs 200 (FIG. 19) used to manipulate different portions the outer frame 42 from an initial deployed state (e.g., circular-like shape) to the desired final deployed state (e.g., an elliptical-like shape). In some embodiments, in the initial deployed state the inner frame 40 and/or the outer frame 42 can have a noncircular-like shape. In some embodiments, in the final deployed state the inner frame 40 may have a noncircular-like shape. In some embodiments, in the final deployed state the outer frame 42 may have a nonelliptical-like shape.

One or more prosthetic valve embodiments disclosed herein may comprise no support arms, a single support arm, a plurality of support arms, support arms with inner and outer support arm members, variations of structures thereof, and/or one more pairs of support arms having various structures and attachment points for providing various functions when implanted. It should be understood that the illustrated embodiments hereof are not limited to the number or configuration of support arms illustrated in each figure and that one or more support arms, one or more pairs of support arms and/or the various structures therefore may be substituted across the various embodiments disclosed herein without departing from the scope hereof.

In one or more embodiments, the prosthetic valves of the present disclosure may comprise one or more support arms for engaging one or more native valve leaflets. In one or more embodiments, valve prosthesis may comprise one or more support arms for engaging one or more native chordae. In one or more embodiments, the prosthetic valve may comprise one or more support arms for engaging one or more native valve commissures. In one or more embodiments, the prosthetic valve may comprise one or more support arms for engaging a native valve annulus. In one or more embodiments, prosthetic valve may comprise one or more support arms for engaging one or more native valve tissues or structures. For example, one or more support arms may engage or interact with valve leaflets, chordae, commissures and/or annulus. In one or more embodiments, the prosthetic valve may comprise one or more support arms for engaging one or more heart tissues or structures. In one or more embodiments, the prosthetic valve may comprise one or more support arms for engaging the pulmonary artery. In one or more embodiments, the prosthetic valve may comprise one or more support arms for engaging the aorta.

In one or more embodiments, one or more support arms may be coupled or connected to a central portion, an inflow portion and/or an outflow portion of the prosthetic valve. In one or more embodiments, the prosthetic valve may comprise one or more support arms that may apply one or more forces such as a radial force, an axial force, a lateral force, an inward force, an outward force, an upstream force, and/or a downstream force to one or more valve structures, valve tissues, heart structures and/or heart tissues. In some embodiments, one or more support arms, as described herein, may be considerably longer, shorter, wider, or narrower than shown. In some embodiments, one or more support arms, as described herein, may be narrower at the base, bottom or proximal end portion where the support arms couple to an inflow portion, central portion and/or an outflow portion of the prosthetic valve and wider at the top or distal end portion of the support arm. In some embodiments, one or more support arms, as described herein, may be wider at the base, bottom, or proximal end portion where the support arms couple to the inflow portion, central portion and/or the outflow portion of the prosthetic valve and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may comprise one or more portions that may extend horizontally, longitudinally, axially, circumferentially, inward, outward, forward, and/or backward. In some embodiments, one or more support arms, as described herein, may comprise more than one configuration. For example, one or more embodiments of one or more support arms, as described herein, may extend in first direction in a delivery, compressed, and/or collapsed configuration and in a second direction in a deployed or expanded configuration. In one example, a first or delivery direction may be a forward direction and a second or deployed direction may be a backward direction. In another example, a first or delivery direction may be a backward direction and a second or deployed direction may be a forward direction. In one or more embodiments, one or more support arms, as described herein, may comprise a first shape in a delivery configuration and a second shape in a deployed configuration. For example, a first or delivery shape may be a straight shape and a second or deployed shape may be a curved shape.

In some embodiments, one or more support arms, as described herein, may comprise one or more portions that comprise one or more spiral shapes, s-shapes, c-shapes, u-shapes, V-shapes, loop shapes, tine shapes, and/or prong shapes. In some embodiments, one or more support arms, as described herein, may comprise a curved, rounded, and/or flared distal end portion. In some embodiments, one or more support arms, as described herein, may be connected, coupled, attached, and/or extend from one or more locations positioned on the inflow portion, the central portion and/or the outflow portion of the prosthetic valve. For example, in some embodiments, one or more support arms, as described herein, may be connected, coupled, attached, and/or extend from one or more locations positioned on the inflow portion, the central portion and/or the outflow portion of the valve prosthesis stent frame support structure. In some embodiments, one or more support arms, as described herein, may comprise at least a portion that may comprise at least one free end not attached or coupled to the stent frame of the prosthetic valve. In one or more embodiments, one or more support arms and/or one or more of components of a support arm may comprise one or more fixation elements or members such as anchors, barbs, prongs, clips, grommets, sutures, and/or screws. In one or more embodiments, one or more support arms and/or one or more of components of a support arm may comprise, for example, one or more active and/or passive fixation elements or members.

In one or more embodiments, the prosthetic valve may comprise an inflow portion, a central portion, and an outflow portion. In one or more embodiments, the prosthetic valve may comprise a single unitary structure or the prosthetic valve may comprise one or more components or portions coupled or connected together. In one or more embodiments, the prosthetic valve may comprise a central portion comprising a valve body, member, or component. In one or more embodiments, the valve body, structure, member, or component may comprise one or more valve leaflets. In one or more embodiments in accordance herewith, the valve leaflets of the valve body, structure, member, or component are attached to an upstream end of the central portion to extend into an inflow portion of the frame, such that the valve body, structure, member, or component is not solely located on or within the outflow portion of the frame. In one or more embodiments, valve member and/or one or more of its components may comprise one or more materials, as described herein.

In one or more embodiments, the central portion of the prosthetic valve and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, an hourglass shape, a polygonal shape, a funnel shape, a nozzle shape, a D-shape, a saddle shape, a planar shape, a non-planar shape, a simple geometric shape, and/or a complex geometric shape. In one or more embodiments, the central portion and/or one or more of its components may comprise one or more fixation elements or members such as anchors, barbs, clips, prongs, grommets, sutures, and/or screws. In one or more embodiments, the central portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the central portion and/or one or more of its components may comprise one or more support arms, components, or members as described herein. In one or more embodiments, one or more support arms may comprise one or more cantilever components or portions. In one or more embodiments, the central portion and/or one or more of its components, such as one or more support arms, may be designed to engage and/or push against the native valve annulus. In one or more embodiments, the central portion and/or one or more of its components, such as one or more support arms, may be designed to engage, capture, clamp, hold, and/or trap one or more native valve leaflets. In one or more embodiments, the central portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the central portion and/or one or more of its components, such as one or more support arms, may be designed to engage and/or push against one or more native valve commissures.

In one or more embodiments, the prosthetic valve may comprise an inflow, inlet, upstream, or proximal portion connected, coupled, positioned, and/or located at a proximal end or proximal end portion of the central portion of the valve prosthesis. In one or more embodiments, the inflow portion and/or one or more of its components may contact, engage, fixate, capture, clamp, pierce, hold, position, and/or seal the prosthetic valve to one or more heart structures and/or tissues such as atrial tissue, ventricle tissue, valve tissue, annulus tissue, the floor of an atrium, and/or the floor of a ventricle. For example, the inflow portion and/or one or more of its components may engage atrial tissue if the prosthetic valve is positioned in a native mitral valve whereas the inflow portion and/or one or more of its components may engage ventricle tissue if the valve prosthesis is positioned in a native aortic valve. In one or more embodiments, the inflow portion and/or one or more of its components may exert one or more forces, for example, radial and/or axial forces, to one or more heart structures and/or heart tissues. In one or more embodiments, the inflow portion and/or one or more of its components may comprise one or more fixation elements or members such as anchors, barbs, clips, prongs, grommets, sutures, and/or screws. In one or more embodiments, the inflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the inflow portion and/or one or more of its components may be designed to deform to the shape of the native anatomy when the prosthetic valve is implanted. For example, the inflow portion may deform from a pre-delivery circular shape to a post-delivery D-shape following the delivery of the prosthetic valve to a native mitral valve. In one or more embodiments, the inflow portion and/or one or more of its components may comprise a frame, a framework, or stent-like structure, as described herein. In one or more embodiments, the inflow portion and/or one or more of its components may comprise, be covered with, be coated with, or be attached or coupled to one or more materials, as described herein. In one or more embodiments, the inflow portion and/or one or more of its components may comprise one or more support arms, components, or members as described herein. In one or more embodiments, one or more support arms may comprise one or more cantilever components or portions. In one or more embodiments, the inflow portion and/or one or more of its components, such as one or more support arms, may be designed to engage and/or push against the native valve annulus. In one or more embodiments, the inflow portion and/or one or more of its components, such as one or more support arms, may be designed to engage, capture, clamp, hold, and/or trap one or more native valve leaflets. In one or more embodiments, the inflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the inflow portion and/or one or more of its components, such as one or more support arms, may be designed to engage and/or push against one or more native valve commissures.

In one or more embodiments, the prosthetic valve may comprise an outflow, outlet, downstream, or distal portion connected, coupled, positioned, and/or located at a distal end or distal end portion of the central portion of the prosthetic valve. In one or more embodiments, the outflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, valve leaflet tissue, annulus tissue, and/or chordae tissue. For example, the outflow portion and/or one or more of its components may engage leaflet tissue, chordae tissue, and/or ventricle tissue if the valve prosthesis is positioned in a native mitral valve whereas the outflow portion and/or one or more of its components may engage leaflet tissue and/or aortic tissue if the valve prosthesis is positioned in a native aortic valve. In one or more embodiments, the outflow portion and/or one or more of its components may exert one or more forces, for example, radial and/or axial forces, to one or more heart structures and/or heart tissues. In one or more embodiments, the outflow portion and/or one or more of its components may comprise one or more fixation elements or members such as anchors, barbs, prongs, clips, grommets, sutures, and/or screws. In one or more embodiments, the outflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the outflow portion and/or one or more of its components may be designed to deform to the shape of the native anatomy when the prosthetic valve is implanted. For example, the outflow portion may deform from a pre-delivery circular shape to a post-delivery D-shape following the delivery of the prosthetic valve to a native mitral valve. In one or more embodiments, the outflow portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the outflow portion and/or one or more of its components may comprise one or more support arms, components, or members as described herein. In one or more embodiments, the outflow portion and/or one or more of its components, such as one or more support arms, may be designed to engage, capture, clamp, hold, and/or trap one or more native valve leaflets. In one or more embodiments, the outflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the outflow portion and/or one or more of its components, such as one or more support arms, may be designed to engage and/or push against one or more native valve commissures. In one or more embodiments, the outflow portion and/or one or more of its components, such as one or more support arms, may be designed to engage and/or push against the native valve annulus. In one or more embodiments, one or more support arms may comprise one or more cantilever components or portions.

In one or more embodiments, the prosthetic valve and/or one or more of its components or portions may comprise, be covered with, be coated with, or be attached or coupled to one or more biocompatible materials or biomaterials, for example, titanium, titanium alloys, Nitinol, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, polyethylene terephthalates, fabrics such as woven fabrics, nonwoven fabrics, porous fabrics, semi-porous fabrics, nonporous fabrics, Dacron fabrics, polytetrafluoroethylene (PTFE) fabrics, polyethylene terephthalate (PET) fabrics, materials that promote tissue ingrowth, rubber, minerals, ceramics, hydroxapatite, epoxies, human or animal protein or tissue such as collagen, laminin, elastin or fibrin, organic materials such as cellulose, or compressed carbon, and/or other materials such as glass, and the like. Materials that are not considered biocompatible may be modified to become biocompatible by a number of methods well known in the art. For example, coating a material with a biocompatible coating may enhance the biocompatibility of that material. Biocompatible materials or biomaterials are usually designed and constructed to be placed in or onto tissue of a patient's body or to contact fluid of a patient's body. Ideally, a biocompatible material or biomaterial will not induce undesirable reactions in the body such as blood clotting, tumor formation, allergic reaction, foreign body reaction (rejection) or inflammatory reaction; will have the physical properties such as strength, elasticity, permeability, and flexibility required to function for the intended purpose; may be purified, fabricated and sterilized easily; will substantially maintain its physical properties and function during the time that it remains in contact with tissues or fluids of the body.

In one or more embodiments, the prosthetic valve and/or one or more of its components or portions may comprise and/or be coupled to or attached to one or more graft materials. In accordance with embodiments hereof, the graft material or portions thereof may be a low-porosity woven fabric, such as polyester, DACRON® polyester, or polytetrafluoroethylene (PTFE), which creates a one-way fluid passage when attached to the stent frame of the valve prosthesis. In an embodiment, the graft material or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for the graft material or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material or portions thereof may be a natural material, such as pericardium or another membranous tissue.

In one or more embodiments, the prosthetic valve and/or one or more of its components or portions may comprise, be coated with, be covered with, be constrained by, or be attached or coupled to a shape memory material, a bioresorbable material, and/or a biodegradable material, such as a natural or synthetic biodegradable polymer, non-limiting examples of which include polysaccharides such as alginate, dextran, cellulose, collagen, and chemical derivatives thereof, proteins such as albumin, and copolymer blends thereof, alone or in combination with synthetic polymers, polyhydroxy acids, such as polylactides, polyglycolides and copolymers thereof, poly(ethylene terephthalate), poly(hydroxybutyric acid); poly(hydroxyvaleric acid), poly [lactide-co-(E-caprolactone)]; poly[glycolide-co-(E-caprolactone)], polycarbonates, poly(pseudo amino acids); poly(amino acids); poly(hydroxyalkanoate)s, polyanhydrides; polyortho esters, and blends and copolymers thereof. In one or more embodiments, one or more surfaces of the valve prosthesis and/or one or more of its components or portions may comprise, be covered with, be coated with, or be attached or coupled to one or more glues and/or adhesives, such as a bioglue or bioadhesive used to help anchor and/or seal the valve prosthesis to native tissue.

In one or more embodiments, one or more surfaces of the prosthetic valve and/or one or more of its components or portions may comprise, be covered with, be coated with, or be attached or coupled to one or more radioactive materials and/or biological agents, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and/or a dye (which acts as a biological ligand). Biological agents may be found in nature (naturally occurring) or may be chemically synthesized by a variety of methods well known in the art.

In one or more embodiments, the prosthetic valve and/or one or more of its components or portions may comprise, be coated with, be covered with, or be attached or coupled to one or more biological cells or tissues, for example, tissue cells, cardiac cells, contractile cells, muscle cells, heart muscle cells, smooth muscle cells, skeletal muscle cells, autologous cells, allogenic cells, xenogenic cells, stem cells, genetically engineered cells, non-engineered cells, mixtures of cells, precursor cells, immunologically neutral cells, differentiated cells, undifferentiated cells, natural tissue, synthetic tissue, animal tissue, human tissue, porcine tissue, equine tissue, porcine tissue, bovine tissue, ovine tissue, autologous tissue, allogenic tissue, xenogenic tissue, autograft tissue, genetically engineered tissue, non-engineered tissue, mixtures of tissues, cardiac tissue, pericardial tissue, cardiac valve tissue, membranous tissue, and/or intestinal submucosa tissue. In one or more embodiments, valve prosthesis and/or one or more of its components or portions may comprise, be covered with, be coated with, or be attached or coupled to one or more materials that promote the growth of cells and/or tissue. In one or more embodiments, the cell and/or tissue promoting materials may comprise, possess or be configured to possess physical characteristics such as size, shape, porosity, matrix structure, fiber structure, and/or chemical characteristics such as growth factors, biological agents, that promote and/or aid, for example, in the adherence, proliferation and/or growth of desired cells and/or tissues in vivo following implantation or ex vivo prior to implantation. In one or more embodiments, the cell and/or tissue promoting materials may accelerate the healing response of the patient following the implantation of the valve prosthesis. In one or more embodiments, the cell and/or tissue promoting materials may comprise pockets, parachutes, voids, and/or openings, for example, that may trap cells and/or tissues and/or promote cells and/or tissues to proliferate, grow and/or heal.

In one or more embodiments, the prosthetic valve may comprise one or more active and/or passive fixation elements or members such as anchors, barbs, prongs, clips, grommets, sutures, and/or screws. In one or more embodiments, one or more active and/or passive fixation elements or members may be delivered separately from the prosthetic valve. In one or more embodiments, one or more active and/or passive fixation elements or members may be delivered before, during, and/or after the prosthetic valve implant procedure. In one or more embodiments, one or more active fixation elements or members may be activated by pushing, pulling, twisting, screwing and/or turning motion or movement. In one or more embodiments, one or more fixation elements or members may be released or engaged via an unsheathing, an unsleeving, a dissolving, and/or a degrading action. In one or more embodiments, one or more active and/or passive fixation elements or members may be delivered using a fixation element delivery system. In one or more embodiments, one or more active and/or passive fixation elements or members may be coupled, connected, and/or attached to the prosthetic valve stent or frame. In one or more embodiments, the prosthetic valve stent or frame may comprise a unitary structure that comprises one or more active and/or passive fixation elements. In one or more embodiments, one or more active and/or passive fixation elements may be coupled, connected, and/or attached to the prosthetic valve skirt and/or graft material. In one or more embodiments, one or more fixation elements or members may be designed to increasingly engage one or more heart tissues and/or structures via any movement of the prosthetic valve relative to heart tissue and/or structures during one or more cardiac cycles. For example, a barbed fixation element that further embeds itself into tissue via movement of the prosthetic valve prosthesis relative to tissue in one direction and then resists movement of the prosthetic valve relative to tissue in the opposite direction.

The prosthetic heart valves of the present disclosure provide a marked improvement over previous designs. By incorporating an adjustable shape (or radial force) feature into the outer frame, along with features that allow a clinician to effectuate shape adjustment, the prosthetic heart valves of the present disclosure can address the non-uniform nature of the native annulus (e.g., a mitral valve annulus) while enabling radial anchoring via transcatheter delivery. The shape or radial force adjustment features of the present disclosure can provide the clinician with an option to address any LVOT or other issues noted during implant. Further, the prosthetic heart valves of the present disclosure allow for variable anatomies to be treated with a smaller number of prosthetic heart valve variations (as compared to conventional prosthetic heart valve designs).

Although the present disclosure has been described with reference to preferred embodiments, workers skilled in the art will recognize that changes can be made in form and detail without departing from the spirit and scope of the present disclosure.

What is claimed is:

1. A prosthetic heart valve comprising:
an inner frame defining an interior volume configured to receive a valve structure within the interior volume;
an outer frame surrounding the inner frame;
wherein the inner and outer frames are each configured to be transitionable between a compressed condition and an expanded condition; and
a connection assembly interconnecting the inner and outer frames;
wherein the prosthetic heart valve is configured to provide an initial deployed state in which the inner and outer frames are in the expanded condition, and further wherein a radial shape of the outer frame in the initial deployed state is adjustable via the connection assembly to a final deployed state.

2. The prosthetic heart valve of claim 1, further comprising a valve structure mounted to the inner frame and disposed within the interior volume.

3. The prosthetic heart valve of claim 1, wherein a hoop strength of the inner frame in the expanded condition is greater than a hoop strength of the outer frame in the expanded condition.

4. The prosthetic heart valve of claim 1, wherein the prosthetic heart valve is configured such that in the initial deployed state, a radial shape of the inner frame remains constant with manipulation of the connection assembly.

5. The prosthetic heart valve of claim 1, wherein the connection assembly includes a plurality of connecting members extending between an exterior of the inner frame and an interior of the outer frame.

6. The prosthetic heart valve of claim 5, wherein a force applied by each of the connecting members onto the outer frame varies as a function of a rotational position of the inner frame relative to the outer frame.

7. The prosthetic heart valve of claim 6, wherein the outer frame has a substantially circular shape in a first rotational arrangement of the inner frame relative to the outer frame, and a substantially elliptical shape in a second rotational arrangement of the inner frame relative to the outer frame.

8. The prosthetic heart valve of claim 1, wherein the connection assembly includes a plurality of arm pairs, each of the arm pairs comprising a first arm projecting outwardly from an exterior of the inner frame and a second arm projecting inwardly from an interior of the outer frame, and further wherein the initial and final deployed states include respective ones of the first arms interfacing with corresponding ones of the second arms.

9. The prosthetic heart valve of claim 8, wherein each of the arm pairs is configured to dictate a radial spacing between the inner and outer frames at a location of the respective arm pair.

10. The prosthetic heart valve of claim 9, wherein the radial spacing generated by a respective arm pair is adjustable.

11. The prosthetic heart valve of claim 8, wherein the first and second arms of each of the arm pairs include complementary engagement features for selectively locking the first arm relative to the corresponding second arm.

12. The prosthetic heart valve of claim 1, further comprising a skirt extending between the inner and outer frames.

13. The prosthetic heart valve of claim 1, wherein the connection assembly includes a component selected from the group consisting of a connecting member and an arm pair.

14. A method of implanting a prosthetic heart valve, the method comprising:
arranging a prosthetic heart valve in a delivery state, the prosthetic heart valve including:
an inner frame defining an interior volume,
a valve structure mounted to the inner frame and disposed within the interior volume,
an outer frame surrounding the inner frame,
wherein the inner and outer frames are each configured to be transitionable between a compressed condition and an expanded condition, and
a connection assembly interconnecting the inner and outer frames;
wherein the delivery state includes the inner and outer frames in the compressed condition;
delivering the prosthetic heart valve through a patient's vasculature to a native heart valve target site;
deploying the prosthetic heart valve at the target site such that the prosthetic heart valve transitions to an initial deployed state in which the inner and outer frames are in the expanded condition; and
adjusting a radial shape of the outer frame from the initial deployed state via the connection assembly to a final deployed state.

15. The method of claim 14, wherein the step of adjusting includes rotating the inner frame relative to the outer frame.

16. The method of claim 15, wherein the connection assembly includes a plurality of connecting members extending between the inner and outer frames, and further wherein a force applied by each of the connecting members onto the outer frame changes with rotation of the inner frame relative to the outer frame.

17. The method of claim 14, wherein the connection assembly includes a plurality of arm pairs, each arm pair including a first arm projecting outwardly from the inner frame and interfacing with a second arm projecting inwardly from the outer frame, and further wherein the step of adjusting includes altering an arrangement of at least one of the arm pairs.

18. The method of claim 17, wherein the step of adjusting includes changing a radial spacing between the inner and outer frames at the corresponding arm pair.

19. The method of claim 17, wherein the step of adjusting includes selectively locking the first arm relative to the corresponding second arm.

20. The method of claim 14, wherein the native heart valve target site is a native mitral valve.

* * * * *